(12) United States Patent
Mik et al.

(10) Patent No.: US 8,008,038 B2
(45) Date of Patent: Aug. 30, 2011

(54) METHODS FOR DETERMINING OXYGEN CONCENTRATION WITH PROTOPORPHYRIN IX

(75) Inventors: Egbert G. Mik, Maasdam (NL); Michiel Sinaasappel, Amsterdam (NL)

(73) Assignee: Academisch Medicsh Centrum bij de Universiteit van Amsterdam, Amsterdam (NL)

( * ) Notice: Subject to any disclaimer, the term of this patent is extended or adjusted under 35 U.S.C. 154(b) by 0 days.

(21) Appl. No.: 12/584,691

(22) Filed: Sep. 10, 2009

(65) Prior Publication Data

US 2010/0255523 A1    Oct. 7, 2010

Related U.S. Application Data

(63) Continuation of application No. 11/988,535, filed as application No. PCT/NL2006/000341 on Jul. 6, 2006, now abandoned.

(30) Foreign Application Priority Data

Jul. 6, 2005    (EP) .................................... 05076565

(51) Int. Cl.
*C12Q 1/02* (2006.01)
(52) U.S. Cl. ........................... 435/29; 436/136; 436/172
(58) Field of Classification Search .................... 435/29; 436/136, 172
See application file for complete search history.

(56) References Cited

U.S. PATENT DOCUMENTS

| 2004/0157905 A1* | 8/2004 | Kennedy et al. ............... 514/410 |
| 2005/0095456 A1* | 5/2005 | Takeda ........................... 428/690 |
| 2009/0130700 A1 | 5/2009 | Leiden et al. |
| 2010/0241197 A1* | 9/2010 | Chang et al. ..................... 607/88 |

FOREIGN PATENT DOCUMENTS

| JP | 2003149152 | 5/2003 |
| WO | WO 93/13403 | 12/1992 |
| WO | WO 93/13403 | 7/1993 |
| WO | WO 01/27585 | 4/2001 |
| WO | WO 2007/004873 A1 | 1/2007 |

OTHER PUBLICATIONS

PCT International Search Report, PCT/NL2006/000341, dated Sep. 11, 2006.
MIK et al., Quantitative determination of localized tissue oxygen concentration in vivo by two-photon excitation phosphorescence lifetime measurements, J. Appl. Physiol., 2004, pp. 1962-69, vol. 97.
U.S. Appl. No. 11/988,535, filed Nov. 13, 2008, Ince et al., Device and Method For Determining The Concentration of a Substance.
Sinaasappel et al., "Calibration of Pd-prophyrin phosphorescence for oxygen concentration measurements in vivo." The American Physiological Society, 1996. pp. 2297-2303.
Lo et al., "Calibration of oxygen-dependent quenching of the phosphorescence of Pd-medo-tetra (4-carboxyphenyl) porphine: A phosphor with general application for measuring oxygen concentration in biological systems." Analytica IBiochemcistry, 1996, pp. 153-160, vol. 236, Article No. 0144.
Kindig et al., "Effect of extracellular $PO_2$ on the fall in intracellular $PO_2$ in contracting single myoctyes," J. Appl Physiol, Jan. 17, 2003, pp. 1964-1970, vol. 94.
Hogan, Michael C., "Phosphorescence quenching method for measurement of intracellular $PO_2$ in isolated skeletal muscle fibers," The American Physiological Society, 1999, pp. 720-724.
Dunphy et al., "Oxyphor R2 and G2: phosphors for measuring oxygen by oxygen-dependent quenching of phosphorescence," Analytical Biochemistry, 2002, pp. 191-198, vol. 310.
Stummer et al., "In vitro and in vivo porphyrin accumulation by C6 glioma cells after exposure to 5-aminolevulinic acid," Journal of Photochemistry and Photobiology B: Biology. 1998. pp. 160-169, vol. 45.
Chantrell et al., "Excited states of protoporphyrin IX dimethyl ester: reaction nfo the triplet with carotenoids." Aug. 26. 1976, pp. 858-865.
Sterenborg, H J C M et al., "A novel frequency domain fluorescence technique for determination of triplet decay times." Phys. Med Biol, 1999, pp. 1419-1426. vol. 44.
Vanderkool et al., "Oxygen in mammalian tissue: methods of measurement and affinities of various reactions." The American Physiological Society, 1991. pp. C1131-C1150.
Erickson et al., "Effect of longitudinal oxygen gradients on effectiveness of manipulation of tumor oxygenation[1,2]," Cancer Research. Aug. 1, 2003, pp. 4705-4712. vol. 63.
Sterenborg et al, "Phosphorescence-fluorescence ration imaging for monitoring the oxygen status during photodynamic therapy," Optics Express. May 3, 2004, pp. 1873-1878. vol. 12. No. 9.
Ziemer et al.. "Oxygen distribution in murine tumors: characterization using oxygen-dependent quenching of phosphorescence," The American Physiological Society, 2005. pp. 1503-1510. vol. 98.
Hartmann et al.. "Non-invasive imaging of tissue $PO_2$ in malignant melanoma of the skin." Melanoma Research. 2006, pp. 479-486. vol. 16. No. 6.
Geissbuehler et al., Triplet imaging of oxygen consumption during the contraction of a single smooth muscle cell (A7r5), Biophysical Journal, Jan. 2010, pp. 339-349. vol. 98.
Heyerdahl et al., "Pharmcokinetic studies on 5-aminolevulinic acid-induced protoporphyrin IX accumulation in tumours and normal tissues," Cancer Letters, 1997, pp. 225-231. vol. 112.
Mik E G et al: "Quantitative determination of localized tissue oxygen concentration in vivo by two-photon excitation phosphorescence lifetime measurements" Journal of Applied Physiology. American Physiological Society 2004. pp. 1962-1969, vol. 97.
Patent Abstracts of Japan vol. 2003, No. 09, Sep. 3, 2003-& JP 2003 149152 A (Igarashi Toshio: Fuji Electric Co Ltd), May 21, 2003.
Mik E G el al., "Mitochondrial oxygen tension within the heart." Journal of Molecular and Cellular Cardiology, 2009, pp. 943-951, vol. 46.

(Continued)

*Primary Examiner* — Ralph Gitomer
(74) *Attorney, Agent, or Firm* — TraskBritt

(57) ABSTRACT

Described are methods and devices for determining a concentration of oxygen in a compartment comprising exciting protoporphyrin IX.

22 Claims, 14 Drawing Sheets

OTHER PUBLICATIONS

Mik E G et al., "In vivo mitochondrial oxygen tension measured by a delayed fluorescence lifetime technique," Biophysical Journal, Oct. 2008, pp. 3977-3990. vol. 95.

Mike G et al., "Mitochondrial $PO_2$ measured by delayed fluorescence of endogenous protophorphyrin IX." Nature Methods Nov. 2006, pp. 939-945, vol. 3, No. 11.

Vanderkool et al., "An optical method for measurement of dioxygen concentration based upon quenching of phosphorescence." The Journal of Biological Chemistry. Apr. 25, 1987, pp. 5476-5482. vol. 262. No. 12.

PCT International Search Report and Written Opinion for International Application No. PCT/NL2006/000341, mailed Sep. 11, 2006.

PCT International Preliminary Report on Patentability for International Application No. PCT/NL2006/000341, mailed Jan. 9, 2008.

Response to European Patent Notification for Application 06757824.5, dated Apr. 22, 2009.

European Patent Office Notification for Application No. 06757824.5 dated Jul. 29, 2010.

European Patent Office Notification for Application No. 06757824.5 dated Oct. 13, 2008.

Submission before oral proceedings and Response to communication dated Jul. 29, 2010 for Application 06757824.5, dated Sep. 28, 2010.

Berg, et al.; Porphyrin-related photosensitizers for cancer imaging and therapeutic applications: Journal of Microscopy, vol. 218. Pt. 2 May 2005: pp. 133-147.

Ericson. et al.: A spectroscopic study of the photobleaching of protoporphyrin IX in solution: Lusers Med. Sci (2003) 18: 56-62.

European Search Report Application No. EP 10 01 2634.1-2204, dated Dec. 7, 2010.

Wilson, et al.; The Oxygen Dependence of Mitochrondrial Oxidative Phosphorylation Measured by a New Optical Method for Measuring Oxygen Concentration; The Journal of Biological Chemistry; Vo. 263, No. 6, Feb. 25, 1983; pp. 2712-2718.

\* cited by examiner porphine    protoporphyrin IX

METHODS FOR DETERMINING OXYGEN CONCENTRATION WITH PROTOPORPHYRIN IX

CROSS-REFERENCE TO RELATED APPLICATIONS

This is a continuation of 11/988,535 filed on Jan. 7, 2008 and accepted on Nov. 13, 2008 now abandoned, which is a national phase entry under 35 U.S.C. §371 of International Patent Application PCT/NL2006/000341, filed Jul. 6, 2006, published in English as International Patent Publication WO 2007/004873 A1 on Jan. 11, 2007, which claims the benefit under Article 8 of the Patent Cooperation Treaty to European Patent Application 05076565.0 filed Jul. 6, 2005, the contents of the entirety of each of which are incorporated herein by this reference.

TECHNICAL FIELD

The invention relates to the field of medicine. More specifically, the invention relates to monitoring the concentration of a substance.

BACKGROUND

Health control, diagnosis of disease and/or monitoring of treatment of disease often involves measurement of various parameters. One parameter is the concentration of a certain substance, such as oxygen, within at least part of an organism. Local tissue oxygenation is an important parameter in the diagnosis and treatment of a wide range of diseases. Measurements of the amount of oxygen present in a specific part of a subject are, for instance, carried out during peri-operative monitoring in the operating room and intensive care and for diagnosis of a wide range of clinical disorders in which tissue oxygenation lies central to the development and cure of disease. Examples include diagnosis of cardiovascular disease, monitoring healing of decubitus and diabetic wounds, monitoring hyperbaric correction of radiation wounds and assessment of success of bypass surgery. Monitoring of tissue oxygen pressure ($pO_2$) during critical illness is considered a major need in the adequate treatment of intensive care patients (Siegemund et al., 1999). Assessment of tumor oxygenation is an example wherein measuring of local tissue oxygenation is helpful for the choice of treatment, as oxygen is an important determinant for success of radiotherapy. Hence, the concentration of oxygen in a tumor is preferably determined in order to determine whether radiotherapy is recommended. Local oxygen measurements are also applicable for the assessment of organ viability for transplantation.

Dioxygen is a molecule of utmost biological importance because of its role as the primary biological oxidant. Therefore, oxygen plays a key role in the oxidation/reduction reactions that are coupled to cellular respiration and energy supply. Adequate measurement of oxygen concentrations in biological samples, such as cells, tissues and whole organs, is important to gain insight in the determinants of oxygen supply and utilization under normal and pathological conditions. It is interesting to note that the clinical interest in methods providing information about blood-flow and oxygen delivery at the organ or sub-organ level (e.g., microcirculatory) is growing. This is, amongst other things, because of increasing insight into the role of the microcirculation in pathogenesis, and the importance of adequate tissue perfusion as end-point of treatment (Siegemund et al., 1999).

Various techniques have been developed for direct or indirect oxygen measurements in tissue, each having its specific advantages and disadvantages (for a review on this subject, see J. M. Vanderkooi et al., 1991). Conventionally, measurements of tissue oxygenation have been made by use of oxygen electrodes and spectrophotometry of the hemoglobin or myoglobin molecule. Reflection spectrophotometry records the difference in absorption and scattering between a standard reference sample and a tissue sample. The method is based on the illumination of a tissue sample by light with a known spectral content and detection of the diffusely reflected light from the tissue at several different wavelengths. The spectral difference between illumination light and detected light contains information about the wavelength-dependent absorption and scattering within the tissue. The reference sample, used for correction of non-ideal apparatus behavior, can be anything with well-known absorption properties, but a white sample (no absorption) is mostly used. The relative tissue absorbency [$E_{r(tissue)}$] can be described by the following equation:

$$[E_{r(tissue)}] = \log(I_{r(standard)}/I_{r(tissue)}) \quad (1)$$

where $I_{r(standard)}$ and $I_{r(tissue)}$ are the intensity of the diffusely reflected light from the white standard and the tissue, respectively. Since the absorption spectra of oxygenated and deoxygenated hemoglobin show marked differences that can easily be detected by RS, this technique is widely used for measurement of hemoglobin saturation in tissue. In order to derive more or less quantitative data with RS, it is necessary to take into account the influence of tissue optical parameters other than the hemoglobin related ones. Different approaches for developing an appropriate analysis algorithm are possible. One described approach is based on the use of isobestic points (the intersection points of the curves of oxygenated and deoxygenated hemoglobin) as reference points within the calculation (Sato, 1979). Dummler used a somewhat different approach for his derivation of an algorithm (Dummler, 1988) based on the two-flux theory of Kubelka and Munk (Kubelka, 1931; Kessler, 1992). The EMPHO, the Erlangen Microlightguide spectrophotometer (Frank, 1989) (EMPHO II, Bodenseewerk Gerätetechnik, Überlingen, Germany) and the O2C (Lea Medizin Technik, Giesen, Germany) are spectrophotometers using improved Dummler algorithms for hemoglobin saturation measurements.

The drawback of these conventional techniques is that they are either mechanically disruptive (insertion of oxygen electrodes) or qualitative (spectrophotometry). These constraints have led to the development of alternative methods. One of the most promising techniques in this respect has been the use of oxygen-dependent quenching of phosphorescent dyes for measurements in the microcirculation (Vanderkooi et al., 1987; Sinaasappel & Ince, 1996; Sinaasappel et. al., 1999).

Wilson and Vanderkooi (Vanderkooi, 1987) introduced the oxygen-dependent quenching of phosphorescence of metallo-porphyrin compounds for biological oxygen concentration measurements. The technique is based upon the principle that a metallo-porphyrin molecule that has been excited by light can either release this absorbed energy as light (phosphorescence) or transfer the absorbed energy to oxygen (without light emission). This results in an oxygen-dependent phosphorescence intensity and lifetime. The relationship between the lifetime and the oxygen concentration is given by the Stern-Volmer relationship (Vanderkooi, 1989). Calibration constants associated with the Stern-Volmer relationship allow oxygen concentrations to be calculated from the measured lifetimes. The measurement of lifetimes allows quantitative measurements without the influence of tissue optical properties.

For in vivo measurements, Pd-porphyrin is bound to albumin to form a large molecular complex that, after injection into the circulation, remains confined, at least for a certain time, inside the blood vessels. This allows microvascular $pO_2$ measurements to be made using a phosphorimeter. A phosphorimeter is a device that measures the phosphorescence decay after a pulse of light (time-domain device) or determines the phase shift between a modulated excitation source and the emitted phosphorescence (frequency-domain device). Several of these systems have been described in literature (Mik, 2002; Coremans, 1993; Sinaasappel, 1996; and Vinogradov, 2002).

Attached to a microscope, phosphorescence lifetime measurements allow the measurement of $pO_2$ in single blood vessels in the microcirculation. Use of fiber phosphorimeters allows measurement of microvascular $pO_2$ ($\mu pO_2$) without having to resort to microscope techniques. A fiber phosphorimeter has been developed for measurement of $\mu pO_2$ in large animal models of shock and sepsis (Sinaasappel, 1999; Van Iterson, 1998), as well as in mice (Van Bommel, 1998), and the analysis of the decay kinetics has been improved to provide more reliable calculation of $pO_2$ values from the decay kinetics (Mik, 2002). A multi-channel implementation of this phosphorimeter allows simultaneous detection of $\mu pO_2$ at different sites and different organs. In general, the use of multi-fiber technology is, besides imaging, a way to detect special information in optical spectroscopy. FIG. 1 schematically shows an example of a frequency-domain phosphorimeter of which the light source is a very cost-effective light-emitting diode (LED).

An advantage of lifetime measurements is the independence of the concentration of the chromophore, making quantitative measurements possible in vivo, where the precise concentration of the chromophore cannot be predicted. An important drawback of this technique is, however, that it relies on injection of palladium-porphyrin into the circulation, making this technique unsuitable for clinical settings because of long-term toxicity. The use is limited to pre-clinical applications. Moreover, this technique is only suitable for measuring oxygen levels in the microcirculation. Since the molecules are large and cell-impermeable, this technique cannot be applied for intracellular oxygen measurements without disrupting the intracellular compartment by micro-injection (Hogan, 1999).

A kind of semi-quantitative oxygen measurement using non-specific protein phosphorescence has been used for oxygen measurements in mitochondrial suspensions. This was based on oxygen-dependent quenching of the phosphorescence of the amino acid tryptophan (Vanderkooi et al., 1990). Unfortunately, this phosphorescence cannot be used for quantitative oxygen measurements because of the complex decay kinetics arising from the different tryptophan-containing proteins (Vanderkooi et al., 1987b). The use of tryptophan phosphorescence for in vivo applications is furthermore limited because of the excitation in the UV region (283 nm), resulting in extremely shallow penetration depths in tissue, besides the well-known photo-toxicity of this high energetic light.

Although both oxygen-dependent quenching of phosphorescence and hemoglobin saturation measurements give information about the microvascular oxygenation status, they do not provide a direct measurement of the adequacy of tissue oxygenation. The latter is highly dependent on factors like tissue oxygen consumption and diffusion distances within the tissue. Additional measurements of, e.g., oxygen extraction and $CO_2$ production are, therefore, often required.

More direct spectroscopic determinations of tissue oxygenation are also possible. One of the oldest, and most widely used, is NADH-fluorimetry. The measurement of tissue bioenergetics is commonly used for measurement of the adequacy of tissue oxygenation. Oxidative phosphorylation occurring in the mitochondria of cells is the main site for the production of ATP. In the final step of the electron transport chain, reduced pyridine nucleotides (NADH) is oxidized to $NAD^+$ and $H_2O$, utilizing molecular oxygen. In contrast to $NAD^+$, NADH emits blue fluorescence (around 450 nm) when illuminated with ultraviolet light (around 360 nm). This allows spectroscopic determination of relative tissue NADH levels. The fluorescence intensity of NADH is, therefore, an optical indicator of cellular metabolism.

Measurement of the fluorescence intensity of endogenous mitochondrial NADH in situ can thus be used as a direct measure of tissue bioenergetics. Since for the conversion of mitochondrial NADH to $NAD^+$ the availability of molecular oxygen is mandatory, lack of oxygen results in accumulation of NADH and subsequent increase in fluorescence intensity. The fluorescence intensity is, for instance, imaged using sensitive photographic or video techniques and can be used to study the regional heterogeneity of tissue dysoxia on organ surfaces in vitro and in vivo. Unwanted influence of the absorbance of hemoglobin can be corrected by use of a two-wavelength method (Coremans, 1997).

However, even with proper calibration, exact quantification of the NADH levels remains impossible (Masters, 1993). One of the reasons is the contribution of cytosolic NADH and NADPH to the total fluorescence signal.

Hence, although oxygen is one of the most important biological molecules, concentration measurements in vivo remain cumbersome. The same kinds of problems arise when the concentration of another substance is measured.

DISCLOSURE OF THE INVENTION

Provided are methods for determining a concentration of a substance.

Provided is a method for determining a concentration of a substance in a compartment comprising:
exciting an endogenous compound of the compartment, or a functional part, derivative, analogue and/or precursor of the compound, wherein the compound, functional part, derivative, analogue and/or precursor, if excited, exhibits a luminescence and/or transient absorption, the lifetime of which is dependent on the substance,
measuring the lifetime of luminescence and/or transient absorption exhibited by the compound, functional part, derivative, analogue and/or precursor, and
correlating the luminescence lifetime with the concentration of the substance.

As described herein, an endogenous compound of an organism, or a precursor, functional part, derivative and/or analogue thereof, is suitable for concentration measurements of a given substance, since it is possible to excite an endogenous compound or a precursor, functional part, derivative and/or analogue thereof in order to exhibit a luminescence and/or a transient absorption, the lifetime of which is dependent on the concentration of the substance. Hence, the lifetime of the luminescence and/or transient absorption is correlated to the concentration of the substance. An endogenous compound is defined as a compound that is naturally present in the compartment, without artificial interference by man, or that is essentially the same kind of compound as a compound that is naturally present in the compartment. Preferably, the compound is identical to a compound that is naturally present in the compartment. In one embodiment, the endogenous compound comprises an administered compound that is essentially the same kind of compound as a compound that is naturally present in the compartment. In another embodiment, the compound is present as a result of a conversion of a precursor into at least one compound that is naturally present in the compartment, or that is essentially the same kind of compound as a compound that is naturally present in the compartment. Hence, in one embodiment, an endogenous compound is derived from a precursor.

It is, of course, possible to provide a compartment with a compound that is the same kind of compound as an endogenous compound. This is, for instance, done to increase the concentration of the endogenous compound. Hence, a method of the invention is not limited to exciting compounds that are already naturally present in a compartment. Exciting an administered compound that is essentially the same kind of compound as an endogenous compound, or that is a functional part, derivative and/or analogue of an endogenous compound, is also within the scope of the present invention. Hence, one embodiment of the invention comprises exciting an endogenous compound, or a functional part, derivative and/or analogue of an endogenous compound, that has been administered to a compartment. Additionally, or alternatively, a method of the invention comprises exciting an endogenous compound that is already naturally present within the compartment. Yet another embodiment of the invention comprises administering a precursor of an endogenous compound that is capable of being converted into at least one endogenous compound, and exciting a compound derived from the precursor. In one embodiment, the precursor is excited.

A functional part of a compound is defined as a part that has the same kind of properties in kind, not necessarily in amount. Preferably, the functional part exhibits a luminescence and/or transient absorption property that is the same, in kind, not necessarily in amount, as the compound. Most preferably, the functional part comprises the same delayed fluorescence and/or triplet-triplet absorption properties as the compound in kind, not necessarily in amount. A "functional derivative of a compound" is defined as a compound that has been altered, such that the luminescence and/or transient absorption properties of the compound are essentially the same in kind, not necessarily in amount. A derivative can be provided in many ways; for instance, by addition, deletion and/or substitution of at least one atom or group, by an esterification, et cetera.

A person skilled in the art is well able to generate analogous compounds. An analogue has essentially the same luminescence and/or transient absorption properties of the compound in kind, not necessarily in amount.

As used herein, the phrase "endogenous compound" also encompasses a functional part, derivative and/or analogue of an endogenous compound.

A "compartment" is defined as an area with properties that make it distinguishable from other areas. The compartment, for instance, comprises an organism as a whole, or a part of an organism, such as, an organ, a tissue, a cell, an organelle, a tumor and/or the microcirculation of an organism, or a part of the organ, tissue, cell, organelle, tumor and/or microcirculation. In a preferred embodiment, the compartment comprises a mitochondrion. In one embodiment, the compartment comprises a part of an organ, tissue or cell. With a method of the present invention, it is possible to measure a concentration of a substance in several parts of an organ, tissue, or cell, such that concentration of a substance at several sites is determined. In one preferred embodiment, a concentration gradient is determined.

In yet another embodiment, the compartment comprises an in vitro compartment, for instance, a culture medium, a cell suspension, a bioreactor or a tissue or organ cultured in vitro. In one embodiment, the compartment comprises an enclosed area, such as an organism, cell, organelle (preferably a mitochondrion) or bioreactor. In an alternative embodiment, the compartment is not enclosed. Examples of such compartments are parts of a tissue, organ and/or tumor. Although no exact borders of such compartment are present, usually tissue present within 20 cm, preferably within 15 cm, of a given site of interest is considered. In one embodiment, the compartment comprises a tumor, because information about the concentration of a substance, such as oxygen, in a tumor is desired in order to determine whether a certain treatment, such as irradiation and/or photodynamic therapy, is suitable. In one preferred embodiment, a concentration gradient through at least part of an organ, wound and/or tumor is determined.

With a method of the invention, it is possible to measure the concentration of any substance capable of influencing a luminescence lifetime and/or transient absorption lifetime of an endogenous compound, or a functional part, derivative, analogue and/or precursor thereof, that has been excited. In a preferred embodiment, the substance comprises oxygen. The invention is further exemplified by the preferred embodiments relating to determination of oxygen concentration. It is to be understood, however, that a method of the invention is also applicable to determining a concentration of another substance capable of influencing a luminescence lifetime of an excited endogenous compound.

In order to determine oxygen concentration within an organism, phosphorescent dyes such as metallo-porphyrins are currently often injected into the circulation. However, as already mentioned, such methods have the disadvantage of long-term toxicity. With a method of the invention, wherein an endogenous compound and/or a precursor thereof is used, this problem is circumvented.

Preferably, a method of the invention is provided wherein the endogenous compound comprises a compound capable of being excited to a triplet state since molecular oxygen is a molecule of which the ground state is a triplet state. Oxygen is, therefore, capable of quenching an excited triplet state. Hence, a compound capable of being excited to a triplet state is particularly suitable for determining an oxygen concentration with a method of the present invention. As used herein, "quenching an excited triplet state" means causing relaxation of an excited triplet state to occur at a rate that is higher than the rate of spontaneous relaxation. "Spontaneous relaxation" means relaxation without the presence of a substance capable of accelerating relaxation. For instance, in the presence of oxygen, the lifetime of an excited triplet state is shortened as compared to the lifetime of an excited triplet state in the absence of oxygen.

Luminescence, for instance, comprises phosphorescence and/or fluorescence. Fluorescence and phosphorescence lifetime measurements are based on the fact that after pulsed excitation, the emitted signal does not vanish instantaneously, but decays with a certain lifetime. Energy transfer between the excited molecules and quencher molecules in its environment causes shortening of the luminescence lifetime. Preferably, luminescence comprises delayed fluorescence. Delayed fluorescence is a phenomenon that occurs in the case of a bi-directional intersystem-crossing. For instance, repopulation of a $S1$ state from a $T1$ state results in delayed fluorescence. Delayed fluorescence presents itself as another component of fluorescence besides prompt fluorescence, having a decay time equal to the lifetime of a triplet state if the time needed for intersystem-crossing is much shorter than the lifetime of the T1 state. Compared to prompt fluorescence, delayed fluorescence is measured much longer after a molecule has been photo-excited, thus avoiding interference of the emitted light pulse and the measured fluorescence.

"Transient absorption" is defined as a temporary absorption change after photoexcitation. Such temporary absorption change is measured using any method known in the art. In one preferred embodiment, transient absorption comprises triplet-triplet absorption. A preferred method of the invention, therefore, comprises measuring a triplet-triplet absorption. This is, for instance, performed with a MicroScan. Triplet-triplet absorption from the first excited Triplet state (T1) to the second excited triplet state (T2) is a process that can only occur after previous population of the first excited Triplet state and during the existence of this T1 state. If, for example, the T1 to T2 transition occurs with the absorption of light of a certain wavelength λ, then a transient absorption of light of wavelength λ is observed after photo excitation of the compound. This transient absorption has a lifetime equal to the T1 lifetime and is, therefore, also a means to measure the T1 lifetime. Triplet-triplet absorption measurements require a second light source (with another wavelength as the main excitation source).

In one aspect of the invention, the endogenous compound comprises a porphyrin. A porphyrin chelated to an iron atom constitutes the heme molecule. Heme is one of the central molecules involved in oxygen transport (hemoglobin and myoglobin) and oxygen utilization (cytochromes in the mitochondrial respiratory chain). Porphyrins are derivatives of porphine. Porphine possesses a ring system (FIG. 2) with four pyrol rings and is a chemically very stable molecule that can be found as "chemical fossil" in oil. Porphine and its derivatives are of biological importance because of their central role in the most vital processes where oxygen turnover takes place. For example, in plants, derivatives of porphine are key substances in the photosynthesis process. This is the process where oxygen is produced out of carbon dioxide and light. In mammals, on the contrary, porphine derivatives like heme and cytochrome C, play central roles in oxygen transport and oxygen consumption.

Preferably, the endogenous compound comprises a protoporphyrin. An even more preferred embodiment provides a method of the invention wherein the compound comprises protoporphyrin IX or a functional part, derivative and/or analogue thereof. Protoporphyrin IX (PpIX) is the final precursor in the synthesis of heme and present in many cells and tissues. Protoporphyrin IX (PpIX, structure formula in FIG. 2) is synthesized inside the mitochondria where it becomes heme after inclusion of an iron atom by the enzyme ferrochelatase. Since the ferrochelatase activity is rather slow (speed limiting step), adding the precursor 5-aminolevulinic acid (ALA) results in a temporary rise in intramitochondrial PpIX levels. Hence, if desired, the level of PpIX in a compartment, such as, a cell and/or tissue, is easily enhanced by administration of 5-aminolevulinic acid (ALA), a precursor of the heme biosynthetic pathway.

Additionally, or alternatively, the level of PpIX in a compartment is enhanced by administration of PpIX. A study of Chantrell et al. reports that PpIX dimethyl ester does not show measurable phosphorescence in the visible range (Chantrell et al., 1977). Therefore, this molecule was not expected to be useful for monitoring a concentration of a substance like oxygen. However, according to the present invention, protoporphyrin IX emits delayed fluorescence after excitation. Protoporphyrin IX possesses an excited triplet state that is quenched by a substance like, for instance, oxygen, making its lifetime dependent on the substance. After excitation of PpIX, delayed fluorescence is observed. Moreover, triplet-triplet absorption is measurable.

A use of a porphyrin or a functional part, derivative and/or analogue thereof for determining a concentration of a substance in a compartment is, therefore, also herewith provided. Porphyrin preferably comprises protoporphyrin IX. In one preferred embodiment, porphyrin comprises a clinically used photodynamic agent, preferably (but not limited to) photofrin, which is currently used for photodynamic therapy against, amongst other things, tumor cells. This provides the advantage that oxygen concentration measurements are possible during therapy with a method of the invention using the therapeutic agent itself.

Without being bound to theory, a working model for state transitions, quenching and measurement modes for PpIX is shown in the Jablonski diagram in FIG. 4. Most often, the population of the triplet state is achieved through excitation of the molecule from the ground state $S_0$ into an excited singlet state ($S_1$ or higher), followed by intersystem crossing from $S_1$ to $T_1$. Because the spontaneous $T_1 \rightarrow S_0$ transition is spin-disallowed, the rate of occurrence is much less than the spin-allowed $S_1 \rightarrow S_0$ transition. This results in relatively long triplet state lifetimes in the order of μs to ms. Molecular oxygen, a molecule of which the ground state is a triplet state, is a quencher of an excited triplet state. If a molecule while it is in the $T_1$ state collides with an oxygen molecule, the oxygen absorbs the energy from the excited molecule. This event results in a relaxation of the excited molecules at a rate higher than the rate of spontaneous relaxation. At sufficiently low concentrations of excited molecules, the relationship between the $T_1$ lifetime and the oxygen concentration is given by the Stern-Volmer relationship:

$$\frac{1}{\tau} = \frac{1}{\tau_0} + k_q[O_2] \quad (2)$$

where τ is the $T_1$ lifetime, $\tau_0$ is the $T_1$ lifetime in the absence of oxygen, and $k_q$ is the rate constant of quenching by oxygen. Quantitative oxygen concentration measurements are possible by means of $T_1$-lifetime measurements.

In general, $T_1$-lifetimes are determined in several ways. In FIG. 4, three different modes of $T_1$-lifetime measurements are shown: phosphorescence, triplet-triplet absorption and delayed fluorescence. In the case of exogenous phosphorescent dyes, phosphorescence lifetimes are measured by measuring the decay of the emitted light after pulsed excitation. However, PpIX does not show measurable phosphorescence (Chantrell et al., 1977). Triplet-triplet absorption relies on the measurement of the transient increase in absorption after photo excitation and population of the triplet state. Triplet-triplet absorption is also suitable for measuring a triplet lifetime of PpIX. One embodiment, therefore, provides a method of the invention wherein measuring the transient absorption lifetime comprises measuring triplet-triplet absorption.

In view of the fact that PpIX does not show measurable phosphorescence, PpIX was not considered in the art to be suitable for monitoring a concentration of a substance like, for instance, oxygen. However, according to the present invention, PpIX is nevertheless suitable since it shows delayed fluorescence and triplet-triplet absorption with an oxygen-dependent lifetime. In contrast to phosphorescence, delayed fluorescence is not red-shifted compared to the prompt fluorescence. Delayed fluorescence of PpIX has not been described in the art.

In vitro studies by the present inventors have shown that PpIX shows a type of delayed fluorescence with a decay time comparable to the decay of the $T_1$ state. The decay of the $T_1$ state was determined by measurement of the light transmission through the sample, the transmission being the reverse of the Triplet-Triplet absorption (FIG. 3, Panels A and B). The sample consisted of a solution of PpIX bound to albumin. Moreover, experiments showed that the decay time of the delayed fluorescence is dependent on the oxygen concentration (FIG. 3, Panel C). FIG. 4 shows a working model for state transitions, quenching and measurement modes.

PpIX is the final precursor in the synthesis of heme used for hemoglobin, myoglobin and cytochromes, all key substances in the transport and/or utilization of oxygen. This makes the use of PpIX as an oxygen sensor even more attractive because it provides a unique method for measurement of an oxygen concentration at the place where the availability of oxygen is the most important (i.e., intracellular and inside the mitochondria). Moreover, delayed fluorescence measurements are easier to implement in vivo and in clinical use than absorption measurements. With a method of the invention, it has become possible to measure the amount of a substance like oxygen directly in a cell and/or organelle, without the need of addition of exogenous, toxic compounds to an organism and without the need to indirectly deduce the concentration from, for instance, the concentration of the substance in the bloodstream or in an intercellular environment.

In one aspect, a method of the invention is provided wherein an endogenous compound or a functional part, derivative, analogue and/or precursor thereof is photo-excited. This is a usual way of exciting a compound and a lot of equipment for photo-exciting is available in the art. An example of a photo-exciting device is described in Shonat et al., 1997, incorporated herein by reference. However, in other embodiments, an endogenous compound or a functional part, derivative, analogue and/or precursor thereof is excited by other means like, for instance, electromagnetic radiation.

Since protoporphyrin IX is naturally present within cells, it has become possible to determine a concentration of a substance, such as, oxygen, within a cell. A method of the invention is, therefore, provided wherein the compartment comprises a cell. In one embodiment, the compartment comprises an organelle. Even more preferably, the compartment comprises a mitochondrion, since protoporphyrin IX is naturally present in mitochondria. Hence, a method of the invention is particularly suitable for determining oxygen concentration in mitochondria. This is a preferred application of the invention since the availability of oxygen in mitochondria is a measure of tissue bioenergetics. Since mitochondria normally consume oxygen, a low concentration of oxygen within mitochondria is indicative for tissue bioenergetics. Tissue bioenergetics is, therefore, preferably assessed by determining a mitochondrial oxygen concentration with a method of the present invention.

One preferred embodiment of the present invention involves determining mitochondrial oxygen concentration after a period of tissue dysoxia in order to determine whether tissue cells are still viable or whether these cells are prone to apoptosis. If a mitochondrial oxygen concentration appears to be low, it indicates that bioenergetics still take place and that the cells are still viable. If, however, mitochondrial oxygen concentrations appear to be high, bioenergetics hardly, if at all, take place indicating that cells are prone to apoptosis. Preferably, 5-aminolevulinic acid is administered to cells, resulting in accumulation of protoporphyrin IX inside the mitochondria. According to this embodiment, luminescence and/or transient absorption lifetime of the accumulated PpIX is measured in order to determine mitochondrial oxygen concentration. Afterwards, a more diffuse fluorescence and/or transient absorption is observed in the cytosol and oxygen concentration throughout the cell is preferably measured. In one preferred embodiment, oxygen concentration in mitochondria of a cell is determined within four hours, more preferably within two hours, even more preferably within one hour after administration of 5-aminolevulinic acid to the cell, because during this period, PpIX primarily accumulates inside mitochondria. In one embodiment, oxygen concentration is determined in other parts of the cell after four hours.

A method described herein is suitable for determining the concentration of a substance such as oxygen in a tissue or organ, or in a certain part of a tissue or organ. Important applications are, for instance, measurements of oxygen concentration in the heart, the brain and/or the retina of the eye, preferably during surgery. Oxygen concentration in the brain and/or heart is, for instance, measured in order to determine whether a stroke and/or myocardial infarction has occurred. In one embodiment, oxygen concentrations in several different parts of a certain tissue or organ are determined in order to obtain an overall impression and/or to measure a $pO_2$ gradient. A method of the invention is, therefore, provided wherein the compartment comprises at least part of a tissue.

Another application of a method of the invention is determination of oxygen concentration at a tumor site. In this embodiment, oxygen concentration within a tumor is determined. Information about oxygen concentration at a tumor site is, for instance, required for determining whether a certain kind of treatment, such as irradiation and/or photodynamic therapy, is suitable. For instance, little oxygen is present at a solid tumor site. Irradiation is, therefore, not likely to be effective at such site. Therefore, once it is determined with a method of the invention that an individual is suffering from a solid tumor with little oxygen, irradiation therapy is preferably not applied. Instead, alternative treatment is preferred. Hence, therapy is adapted to information about oxygen concentration, which information is obtained by a method of the invention. In a further embodiment, oxygen concentration at a tumor site and/or around a tumor site is monitored with a method of the invention in order to monitor progress of disease and/or therapy.

In one embodiment, a concentration of a substance, such as oxygen, at a location of interest is measured by providing an organism with an endogenous compound, and/or with a precursor thereof, which is coupled to a moiety capable of specifically binding the location of interest. The moiety, for instance, comprises an antibody or a functional part, derivative and/or analogue thereof. For instance, if the oxygen concentration in a tumor is to be measured, an endogenous compound or a precursor thereof is preferably coupled to an antibody capable of specifically binding a tumor-specific antigen. A tumor-specific antigen is an antigen that is present on a tumor cell while it is less (preferably not) present on normal cells. The endogenous compound or precursor coupled to a tumor-specific antibody will accumulate in and/or around the tumor. This results in an increased concentration of the endogenous compound and/or precursor in and/or around the tumor, facilitating oxygen concentration measurement in and/or around the tumor. Likewise, in other embodiments, the concentration of a substance is specifically measured at any location of interest, using an endogenous compound and/or precursor thereof that is coupled to a moiety capable of specifically binding the location of interest.

In yet another aspect, an endogenous compound such as a porphyrin, preferably protoporphyrin IX, is administered to the circulation of an individual. Alternatively, or additionally, a precursor is administered that is converted in vivo into at least one metabolite that is essentially the same kind as, and preferably identical to, an endogenous compound and that, if excited, exhibits a luminescence and/or transient absorption of which the lifetime is dependent on the concentration of a given substance. In one embodiment, 5-aminolevulinic acid is administered, which is metabolized into protoporphyrin IX in vivo. When an endogenous compound or a precursor thereof is administered to the circulation of an individual, the molecule is in one embodiment bound, for instance, to albumin, to form a large molecular complex that remains confined, at least for a certain time, inside the circulation. The administered compound, which is essentially the same kind as an endogenous compound, and/or whose metabolite is essentially the same kind as an endogenous compound, is not or to a lesser extent toxic as compared to exogenous compounds, for instance, palladium-porphyrin. Administration of the compound is, therefore, not, or to a lesser extent, involved with (harmful) side effects. In one embodiment, a method of the invention is, therefore, provided wherein the compartment comprises the (micro) circulation.

Another application of a method of the invention is the use of an endogenous compound or a functional part, derivative, analogue and/or precursor thereof, for determining the concentration of a substance in a culture medium. In one embodiment, a certain kind of tissue, cell and/or organism is cultured in a culture medium. In order to determine the concentration of a substance within the tissue, cell and/or organism, an endogenous compound of the tissue, cell and/or organism or a functional part, derivative, analogue and/or precursor thereof is excited. Subsequently, the lifetime of luminescence and/or transient absorption is measured. In one embodiment, the culture medium comprises a cell suspension.

It is possible to administer to the culture medium a suitable compound which, when excited, displays a luminescence and/or transient absorption, the lifetime of which is dependent on the concentration of a certain substance, or a compound that is converted in vivo into at least one metabolite that is essentially the same kind as, preferably identical to, an endogenous compound. The administered compound, for instance, comprises a compound that is essentially the same kind as, preferably identical to, an endogenous compound. However, the compound need not be naturally present in the cultured tissue, cell and/or organism. In one embodiment, a porphyrin, preferably protoporphyrin IX, or a precursor thereof, such as, 5-aminolevulinic acid, is administered to a culture medium, such as a bioreactor, in order to monitor oxygen concentration with a method of the invention, comprising exciting the porphyrin and measuring the lifetime of delayed fluorescence. Preferably, the oxygen concentration is measured at several time points, such that the availability of oxygen is monitored over time.

In a preferred embodiment, the lifetime of luminescence and/or transient absorption is compared with a reference curve. A reference curve (also called a calibration curve) is, for instance, generated, from which kq and $\tau_0$ are derived. Once kq and $\tau_0$ are determined, a luminescence lifetime is correlated with the concentration of a substance, preferably by the Stern-Volmer relationship. Additionally, or alternatively, a reference curve is preferably generated in order to correlate the lifetime of transient absorption to the concentration of a given substance. In one embodiment, a compartment is successively provided with various concentrations of a substance in order to generate a reference curve. Additionally, or alternatively, several similar compartments are provided with various concentrations of a substance. According to this embodiment, luminescence and/or transient absorption lifetime is determined at various concentrations of the substance. Many alternative methods of generating a reference curve are known in the art, which are suitable for a method of the present invention.

In order to generate a reference curve, a luminescence and/or transient absorption lifetime is preferably determined at least two concentrations of the substance. Preferably, however, luminescence and/or transient absorption lifetime is determined at least three concentrations of the substance, more preferably at least four concentrations of the substance. The more luminescence and/or transient absorption lifetime vs. substance concentration values are measured, the more accurate a reference curve will be. A reference curve is, for instance, generated by plotting luminescence lifetime and/or transient absorption lifetime versus concentration of a substance. Of course, the reference curve need not to be physically plotted. It is, for instance, also possible to store measured reference values, for instance, in a (computer) database. A formula representing a reference curve is, for instance, calculated. In one embodiment, a measured luminescence lifetime and/or transient absorption lifetime is entered into the database, after which an algorithm calculates and discloses the correlated substance concentration.

Preferably, a calibration curve is generated using the same kind of compartment(s) as the compartment(s) wherein the concentration of at least one substance is to be measured. Moreover, the reference curve is preferably generated using the same kind of substance(s) as the substance(s) whose concentration(s) is/are to be measured. Once a calibration curve is generated, it is preferably used to correlate a measured luminescence and/or transient absorption lifetime with a concentration of a substance. In one embodiment, a calibration curve is generated before the concentration of a substance in a compartment is determined. However, once a calibration curve has been generated, it is not necessary to generate another calibration curve each time before a concentration of a substance is determined. For instance, once kq and $\tau_0$ have been determined, it is preferably repeatedly used for correlating the lifetime to the concentration of a certain substance.

In one aspect of the invention, a luminescence lifetime is measured in the time domain, meaning that the lifetime is measured after a pulse of light. In another aspect, the lifetime is measured in the frequency domain, meaning that continuous excitation takes place. The phase shift between a modulated excitation source and the emitted luminescence is measured. For instance, phosphorescence and/or delayed fluorescence is/are capable of being measured in the frequency domain. Measurement of the lifetime in the frequency domain is usually cheaper. On the other hand, measurement of the lifetime in the time domain is possible with a higher intensity of light.

A method of the invention is suitable for being performed with single-photon excitation. However, a preferred embodiment provides a method of the invention wherein multi-photon excitation is applied, for instance, two-photon, three-photon or four-photon excitation. Multi-photon excitation involves excitation with multiple photons instead of one. The multiple photons, for instance, have one-half of the energy of a single photon (in case of two-photon excitation). The multiple photons have one-third of the energy of a single photon (in case of three-photon excitation), or one-fourth of the energy of a single photon (in case of four-photon excitation), and so on. Multi-photon excitation is preferred because it allows for deeper tissue penetration and a more precise and confined selection of an excitation volume as compared to single-photon excitation, due to the non-linear multi-photon effect. Hence, with multi-photon excitation, inner parts of a compartment, such as, inner parts of a tissue or organ, are more easily examined. Multi-photon excitation facilitates determination of a concentration gradient, for instance, from an outer surface of a tissue until an inner part of such tissue or vice versa. Moreover, since multi-photon excitation allows for a more precise and confined selection of an excitation volume, damage to surrounding tissue is more easily avoided.

In one preferred embodiment, a method of the invention is used for an "optical biopsy." This means that a certain part of interest, such as a small part of a certain tissue, is investigated but not excised. A characteristic, for instance, an oxygen concentration of the part of interest, is determined using a method of the invention specifically directed to the part of interest, while the part of interest remains at its original site. For instance, at least part of a tissue of an organism is investigated while the part remains in the organism. This is preferably performed using multi-photon excitation because multi-photon excitation allows for a precise selection of an excitation volume.

In a preferred embodiment, two-photon excitation is applied. The principles and advantages of two-photon excitation are outlined in Mik (2004), which is incorporated herein by reference. In contrast to single-photon excitation, two-photon excitation is a non-linear optical process in which a compound is excited by two photons instead of a single photon with a double energy (or half the wavelength). By considering the excitation as the rate-limiting step in a chemical reaction consisting of a single-step termolecular process involving one molecule and two photons, one derives the rate of production of excited-state molecules, $R_{TPE}$:

$$R_{TPE} = \frac{\delta}{2} \frac{1}{A} - CP^2 \quad (3)$$

where $\delta$ is the two-photon cross-section, l the path length, A the cross-sectional area of the beam (multiplying l by A defines the interaction volume), C the molar concentration of the excitable compounds and P the power of the excitation beam. In phosphorescence measurements, the intensity of the signal is proportional to $R_{TPE}$, therefore, equation (3) can be rewritten in terms of signal intensity versus excitation power:

$$I_0 \propto CP^2 \quad (4)$$

where $I_0$ is the measured phosphorescence intensity at time zero, i.e., directly after the excitation pulse. In equation 4, constants influencing the absolute value of $I_0$, like the molecular constants, excitation geometry and detection efficiency are omitted. These constants are intensity independent so that the proportionality sign describes the relation between $I_0$ and $P^2$. The non-linear behavior of TPE provides a means of selective excitation within a three-dimensional space, and the quadratic dependence of emission intensity versus excitation power is regarded as proof of the two-photon nature of the studied phenomena.

The invention furthermore provides a device for determining a concentration of a substance in a compartment comprising:
  means for exciting an endogenous compound or a functional part, derivative, analogue and/or precursor thereof, wherein the compound, part, derivative, analogue and/or precursor, if excited, exhibits a luminescence and/or transient absorption of which the lifetime is dependent on the substance, and
  means for measuring the lifetime.

Preferably, equipment for optical spectroscopy comprises an illumination light source, an optical system (for instance, comprising filters, mirrors and lenses) and a detection unit. The detector, for instance, comprises a sensitive CCD camera, photomultiplier tube and/or spectrophotometer. Several descriptions of optical systems are described in the literature (Carlsen et al., 2002; Baxter et al., 1997; Green et al., 1988). An example of a frequency domain phosphorescence lifetime measurement device is described in Shonat et al., 1997, incorporated herein by reference. Non-limiting examples of a device of the invention are outlined in the Examples. In a preferred embodiment, a combination of a prism and a bandpass filter is used, at least partly preventing a high amount of excitation light to reach the filters in order to avoid possible disturbance of a delayed fluorescence signal as a result of fluorescence and/or phosphorescence of the filters themselves. In a further preferred embodiment, a device of the invention comprises a fast shutter in front of a PMT, preferably a pockel cell, in order to prevent distortion of the first 20 to 30 µs of a signal, which would otherwise occur if a PMT is gated by switching the voltages of the second and third dynodes during the laser pulse. Alternatively, a semiconductor device, preferably an avalanche-photodiode, is used, which is cheaper.

In one preferred embodiment, a device according to the invention comprising an imaging device capable of oxygen mapping, preferably a CCD camera and/or a diode array, is used in order to allow imaging of a specific location.

Reference measurements are preferably performed for quantitative measurements in order to take account of possible influences of tissue optical properties on the signal.

DETAILED DESCRIPTION OF THE INVENTION

Figure 1:
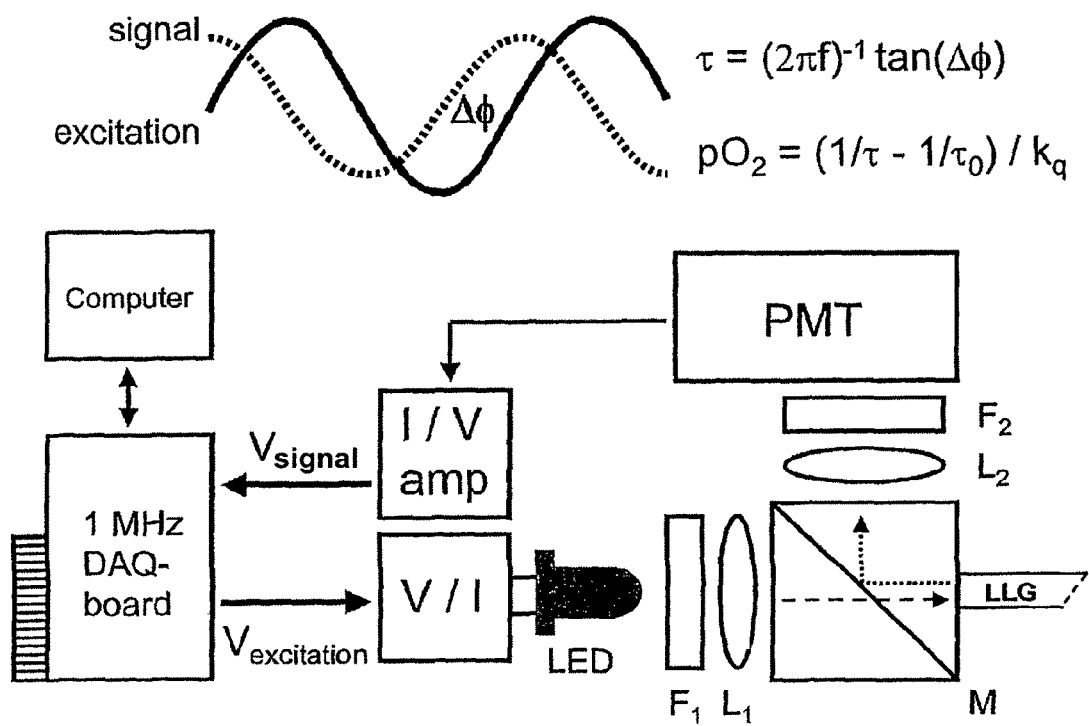
FIG. 1: Schematic example of frequency-domain phosphorimeter. A sinusoidal voltage ($V_{excitation}$) with a frequency of 2000 Hz is generated by a data acquisition board (PCI-MIO-16E1, National Instruments). The light output of the green LED is modulated by $V_{excitation}$ through a voltage-to-current converter. The excitation light is filtered by a 530 broadband bandpass filter (F1) and focused into a liquid light guide (LLG, Oriel) by a lens (L1). The emission light returning from the sample is directed to the detector by a dichroic mirror (M). L2 is a coupling lens and F2 is a 700 nm bandpass filter. The detector is a red-sensitive photomultiplier tube (PMT, Hamamatsu R928). The current from the PMT passes a current-to-voltage converter and is amplified to generate a signal ($V_{signal}$) that can be sampled by the DAQ-board. The phase shift between $V_{excitation}$ and $V_{signal}$ is determined by software, for instance, written in LabView (such as version 5.1, National Instruments). The phosphorescence lifetime ($\tau$) is calculated from $\Delta\Phi$, allowing the calculation of the oxygen tension ($pO_2$) by the Stern-Volmer relationship, with $\tau_0$ the lifetime under zero-oxygen conditions and $k_q$ the quenching constant.
Figure 2:
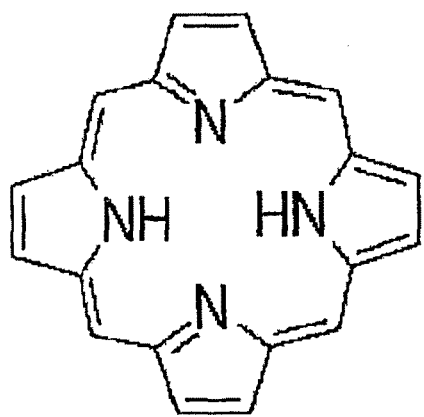
FIG. 2: Structure formulas of porphine and protoporphyrin IX.
Figure 2:
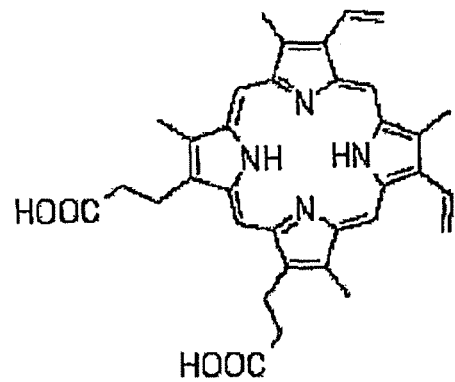
Figure 3:
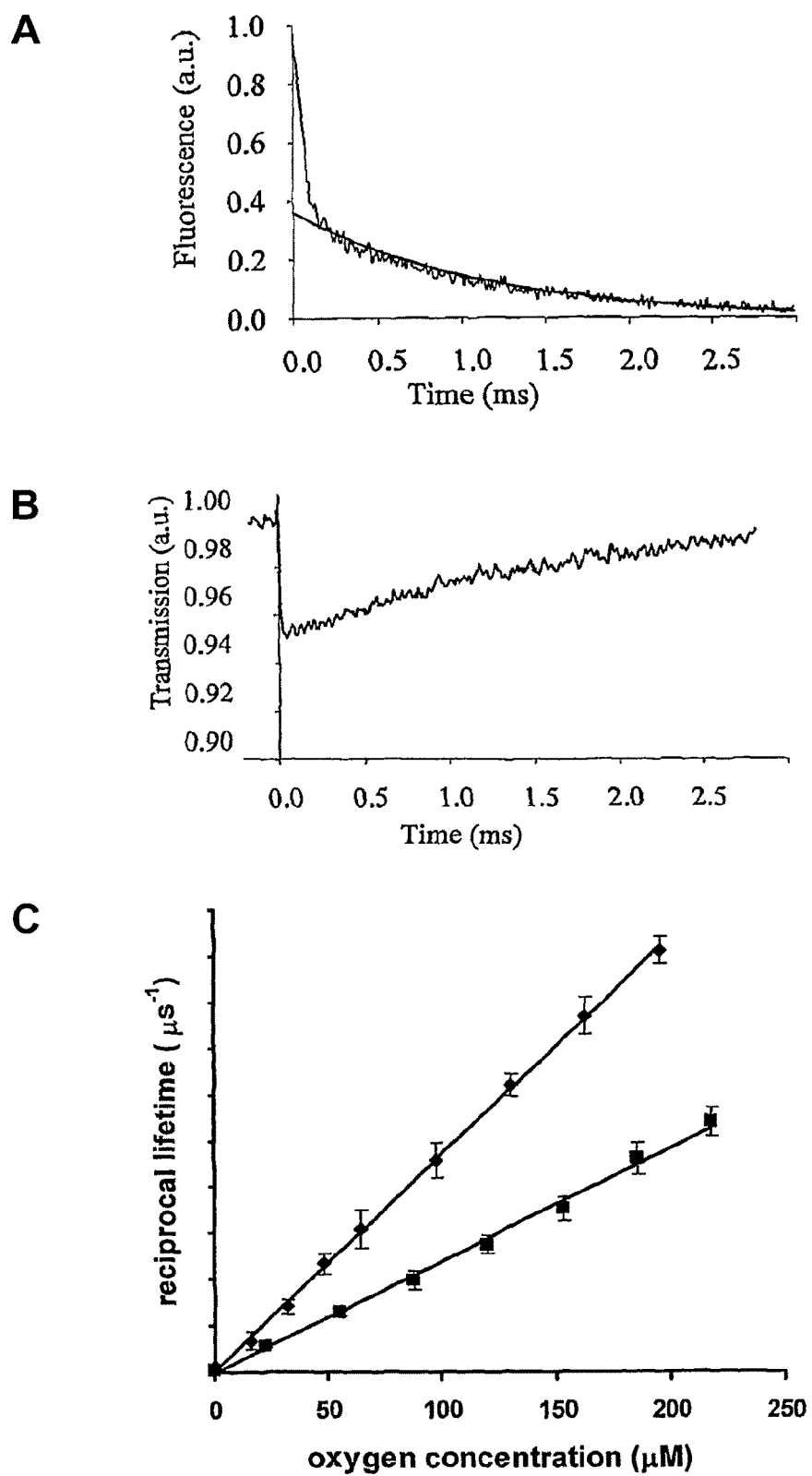
FIG. 3: Panel A: The delayed fluorescence at zero oxygen conditions measured in a solution of PpIX bound to albumin. Panel B: The Triplet-Triplet absorption at 470 nm also at zero oxygen, same sample as A. Panel C: Reciprocal lifetime of delayed fluorescence as a function of oxygen concentration at two different temperatures.
Figure 4:
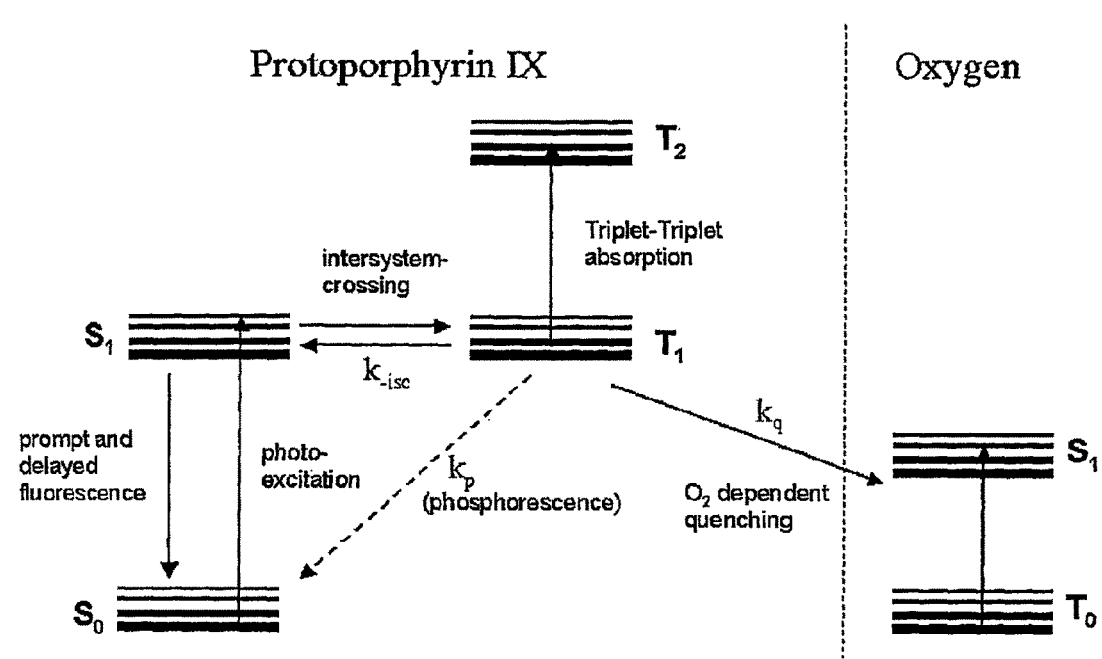
FIG. 4: Jablonski diagram showing, schematically, the energy states and state-transitions of PpIX and its interaction with dioxygen. $S_0$-$S_2$ denote singlet states. $T_0$-$T_2$ denote triplet states. $K_q$ and $k_p$ are the rate constants of the occurrence of quenching and phosphorescence, respectively. In the diagram, parentheses and the broken arrow depict the absence of detectable phosphorescence. $K_{-isc}$ is the rate constant of the $T_1 \rightarrow S_1$ intersystem crossing.

The invention is further described by the following illustrative examples.

EXAMPLES

Example 1

The spectra of prompt and delayed luminescence were recorded using a LS50B luminescence spectrometer (Perkin-Elmer, Wellesley, Mass., USA). Prompt fluorescence was measured using the fluorescence mode with excitation source correction. Delayed luminescence was recorded in the phosphorescence mode, using varying delay times with respect to the excitation flash and a gate width of 100 μs. The measurements were made at room temperature. Excitation and emission wavelengths and slit widths will be specified in the results section. Spectra were recorded with either air-saturated samples or samples containing zero oxygen. Adding a sufficient amount of ascorbic acid (20 μl of 200 mM solution) to the already ascorbate oxidase-containing samples (1 unit ascorbate oxidase per ml, 3 ml total sample volume) created the zero-oxygen conditions. This method of reducing oxygen levels is explained in more detail below. The amounts of ascorbate oxidase and ascorbic acid used did not interfere with the readings of the spectra.

The experiments concerning comparison of triplet-triplet absorption kinetics with delayed fluorescence lifetimes, and the measurement of transient absorption spectra, were performed using an LFDL-3/Remote flash lamp pumped dye laser (Candela Laser Corporation, Wayland, Mass.). This system provided pulses with a duration of approximately 1 μs at 505 nm at a repetition frequency of 10 Hz. The output of the laser was directly focused on the sample, consisting of a quartz cuvette containing the PpIX solution. The used detector was a R928 (HAMAMATSU, Hamamatsu City, Japan) photomultiplier tube (PMT) with a C1392-09 (HAMAMATSU, Hamamatsu City, Japan) gated socket. The detector was coupled to a monochromator (Oriel 77320) in order to select the emission wavelength of interest. The output of the PMT was fed into an oscilloscope (Tektronix 2440, TEKTRONIX INC., Beaverton Oreg., USA) and transferred to a computer by the serial bus. The wavelength-dependent transient absorption was measured using a white light source and scanning of the monochromator. These experiments were carried out at room temperature (20° C.).

Calibration experiments with varying oxygen concentrations were performed with a different set-up. An XeCl excimer laser (Lambda Physik LPX 110i, Göttingen, Germany), operated at 10 Hz and producing 50 mJ pulses, was used to pump a dye laser (Lambda Physik, LPD 3002) operating at 405 nm. The output of the dye laser was focused on a quartz optical fiber with a core of 0.6 mm (Ensign Bickford Optics, Avon, Conn.) using a 3 cm F/1.2 quartz lens. The fiber was coupled to the reaction vessel (described below) used for the calibration experiments. The detector was the same R928PMT with C1392-09 socked, switched off during 5 μs gate width. The detector was coupled to the reaction vessel by a VIS-type liquid light guide with a 5 mm optical core (Oriel, Stratford, USA). Instead of the monochromator, three 630 nm long pass glass filters were used for filtering of the emission light. The laser pulse was fired 1 μs after off gating of the PMT; the repetition rate was 10 Hz. Per measurement, 64 traces were averaged on a digital oscilloscope (Tektronix TDS-350, Tektronix Inc., Beaverton Oreg., USA). Data were transferred to a computer by serial bus and lifetime analysis was performed using LabView 5.1 graphical programming software (National Instruments, Austin, Tex., USA). Monoexponential fitting was performed using a Marquard-Levenberg non-linear fit.

To perform delayed fluorescence lifetime measurements at varying oxygen concentrations, the oxygen concentration in the PpIX solution was varied using the ascorbate oxidase/ascorbic acid enzymatic reaction. Calibration experiments, needing precisely controlled oxygen concentrations, were performed using a specially made reaction vessel. The vessel had to be airtight, allow continuous mixing of the PpIX solution, temperature control, continuous temperature monitoring and physical access to the content. The latter was necessary to allow injection of aliquots of ascorbic acid solution but should not go at the expense of an interfering oxygen back-diffusion into the sample. It consisted of two glass parts, a bottom part and a top part. Both parts were interconnected by screw lock. An airtight connection was assured by a TEFLON® ring surrounding the connection site. The bottom of the reaction vessel was flat to allow continuous stirring of the content by a magnetic stirrer. The top part contained three capillary entries: one allowing insertion of a small thermocouple, one for the insertion of the light guide from the excitation source and the latter for injection of ascorbic acid. The capillaries had a length of 2 cm and a lumen of 1 mm diameter. The diffusion barrier was large enough to prevent measurable oxygen back-diffusion within an hour, an adequate time span for calibration experiments. This was checked by oxygen-dependent quenching of phosphorescence of Pd-meso-tetra(4)-carboxyphenyl porphine starting at varying oxygen concentrations below 40 µM. The reaction vessel was mounted in a temperature-controlled water jacked on top of a magnetic stirring device. The total content of the reaction vessel, after insertion of the magnetic stirrer, was 30.7 ml. Injection of 10 µl of a 200 mM solution of ascorbic acid resulted, therefore, in 32.5 µM oxygen steps ($PO_2$ steps of approximately 20 mmHg). Prior to the experiments, the reaction vessel was filled with pre-heated, room-air equilibrated PpIX solution. Special care was taken to remove all air bubbles from the solution. Calibration experiments were performed at 22° C. and 37° C.

Chemicals

Pd-meso-tetra(4)-carboxyphenyl porphine was purchased from Porphyrin Products (Porphyrin Products Inc., Logan, Utah, USA). Protoporphyrin IX disodium salt (PpIX) was purchased from Sigma (Sigma Chemical Co., St. Louis, Mo., USA). Two regimens of creating PpIX solutions were used. In the first regimen, 8 mg/ml PpIX was dissolved in distilled water brought at a pH of 8.0 by titration with 1 M TRIS base. From this solution, 0.5 ml was added to 50 ml of a human albumin solution (40 gr/l) in phosphate-buffered saline (PBS). This mixture was brought to a pH of 7.4 by titration with HCl. The PpIX is dissolved in an albumin solution to obtain a complex, mimicking the environmental circumstances in cells and tissue (Takemura et al., 1991). The experiments concerning triplet-triplet absorption were performed with PpIX solution prepared following this protocol. Since dissolving PpIX according to the protocol above takes rather long (PpIX is usually not completely dissolved after several hours), during the course of the study we looked for a more efficient way of preparing the PpIX solutions. In the second regimen, 4.0 grams of bovine serum albumin (BSA, Sigma Chemical Co., St. Louis Mo., USA) was dissolved in 200 ml PBS. To increase the buffer capacity needed to prevent pH changes when adding aliquots of ascorbic acid to the solution, 800 mg HEPES was added. PpIX was dissolved in methanol (6.07 mg PpIX in 10 ml methanol) and 2 ml of this PpIX solution was immediately added to the albumin solution, resulting in a final concentration of approximately 10 µM PpIX. PpIX solutions according to the second regimen were used for the recording of the shown spectra and calibration experiments, unless stated otherwise.

Results

Figure 5:
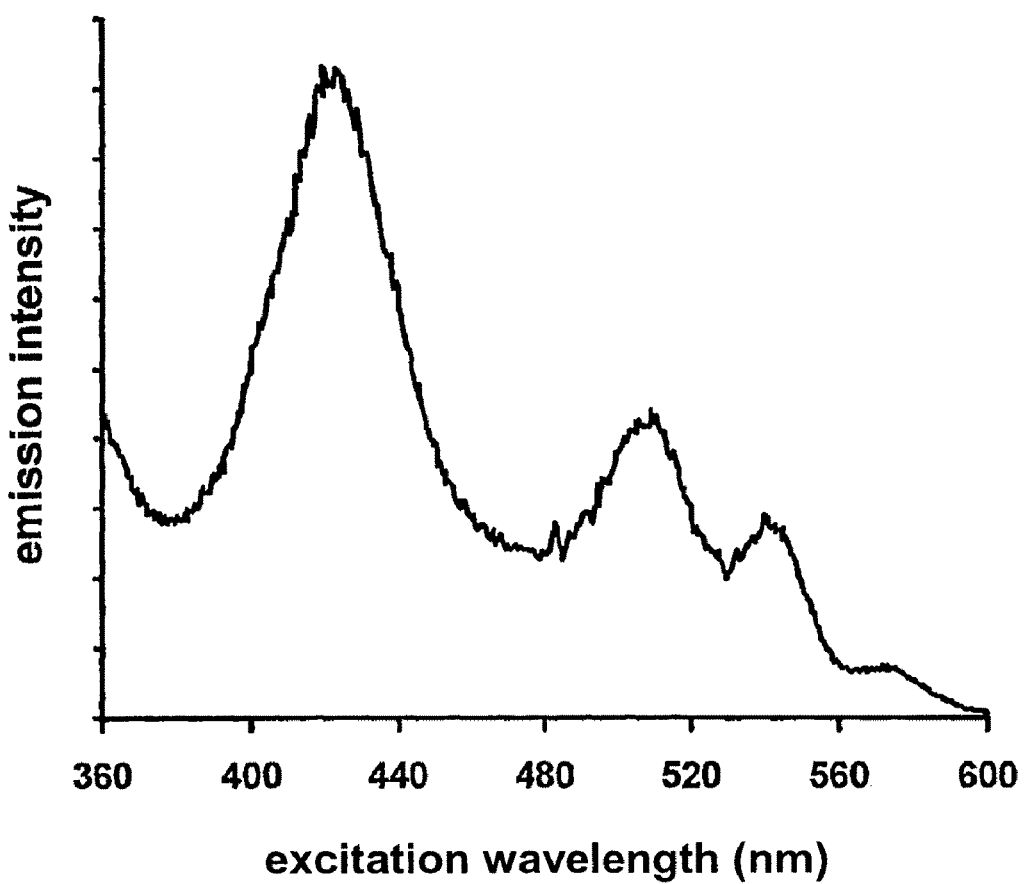
FIG. 5: Emission intensity of PpIX fluorescence as a function of the excitation wavelength.

Metallo-porphyrins used for oxygen concentration measurements in vivo can usually be effectively excited at several different wavelengths. For example Pd-porphyrin, the most widely used phosphorescent dye for in vivo measurements, can be effectively excited around 400 nm (the Soret maximum) and 530 nm (the Q-band). Generally, light with a longer wavelength penetrates deeper into tissue, the reason why usually excitation at 530 nm is favored for in vivo measurements, although the excitation efficiency at 400 nm is much higher. FIG. 5 shows the fluorescence emission versus the excitation wavelength of PpIX bound to albumin. Two peak emissions, one around 400 nm and one around 510 nm, are prominently present. The excitation wavelengths of the used lasers are indicated in the figure for convenience. As will become apparent, both wavelengths are effective for delayed fluorescence measurements.

Figure 6:
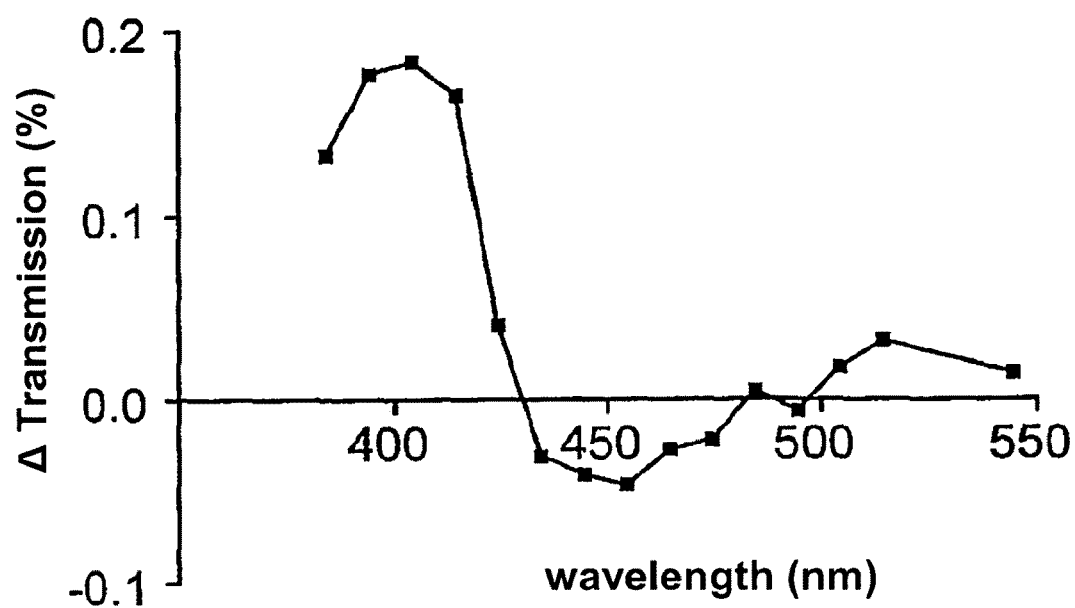
FIG. 6: The transient transmission of 20 μM PpIX in 4% albumin as a function of the transmission wavelength after pulsed excitation at 505 nm. The maximum at 400 nm is caused by depletion of the ground state by the laser pulse, the minimum at 450 nm is due to population of the $T_1$ level and absorption to the $T_2$ level.

In order to locate an appropriate wavelength for triplet-triplet absorption measurements, the transient transmission spectrum was recorded. FIG. 6 shows the transient transmission spectrum of a 20 µM PpIX solution as A function of the transmission wavelength. The maximum at 400 nm is caused by depletion of the ground state by the laser pulse, the minimum at 450 nm is due to population of the $T_1$ level and absorption to the $T_2$ level. These results are in good agreement with previous studies (Chantrell et al., 1977; Bonnett et al., 1983; Sinclair et al., 1980).

Figure 7:
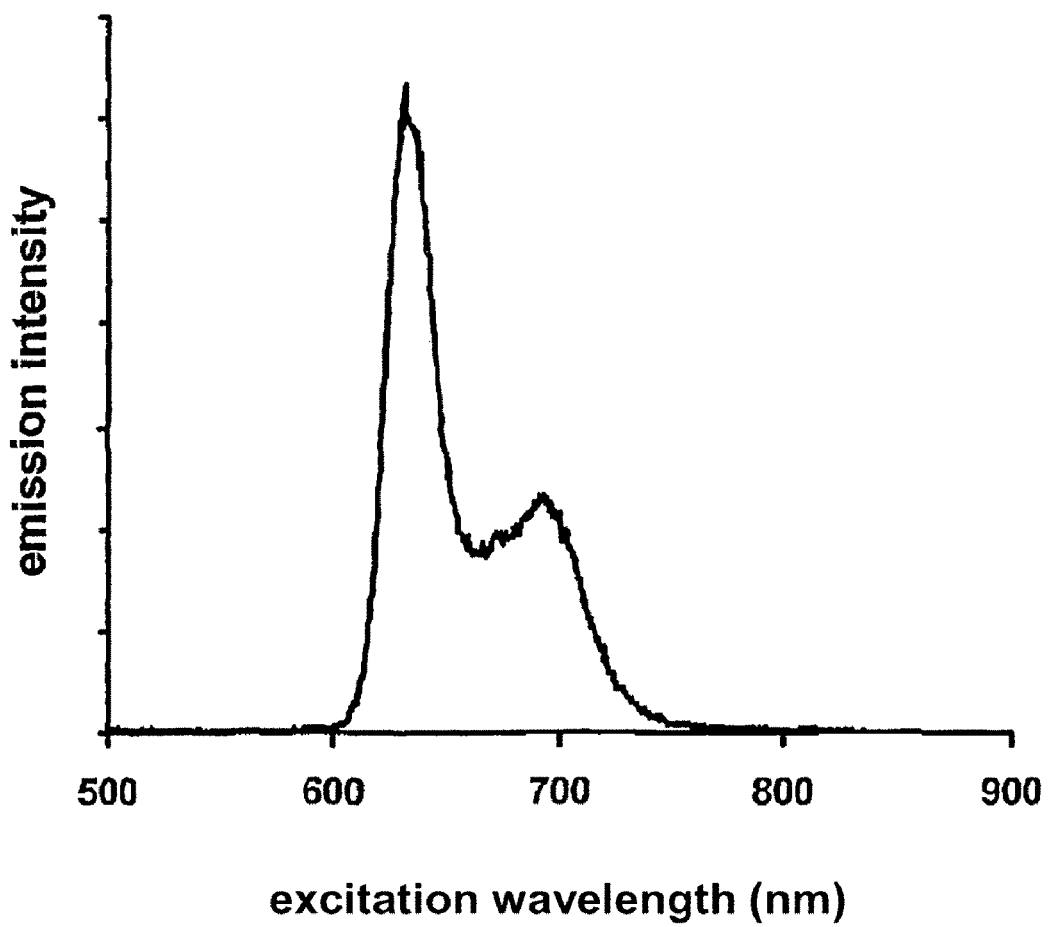
FIG. 7: Prompt fluorescence emission spectrum of PpIX bound to albumin. Excitation wavelength was 405±2.5 nm. The emission was detected with a 4 nm slit width of the monochromator.
Figure 8:
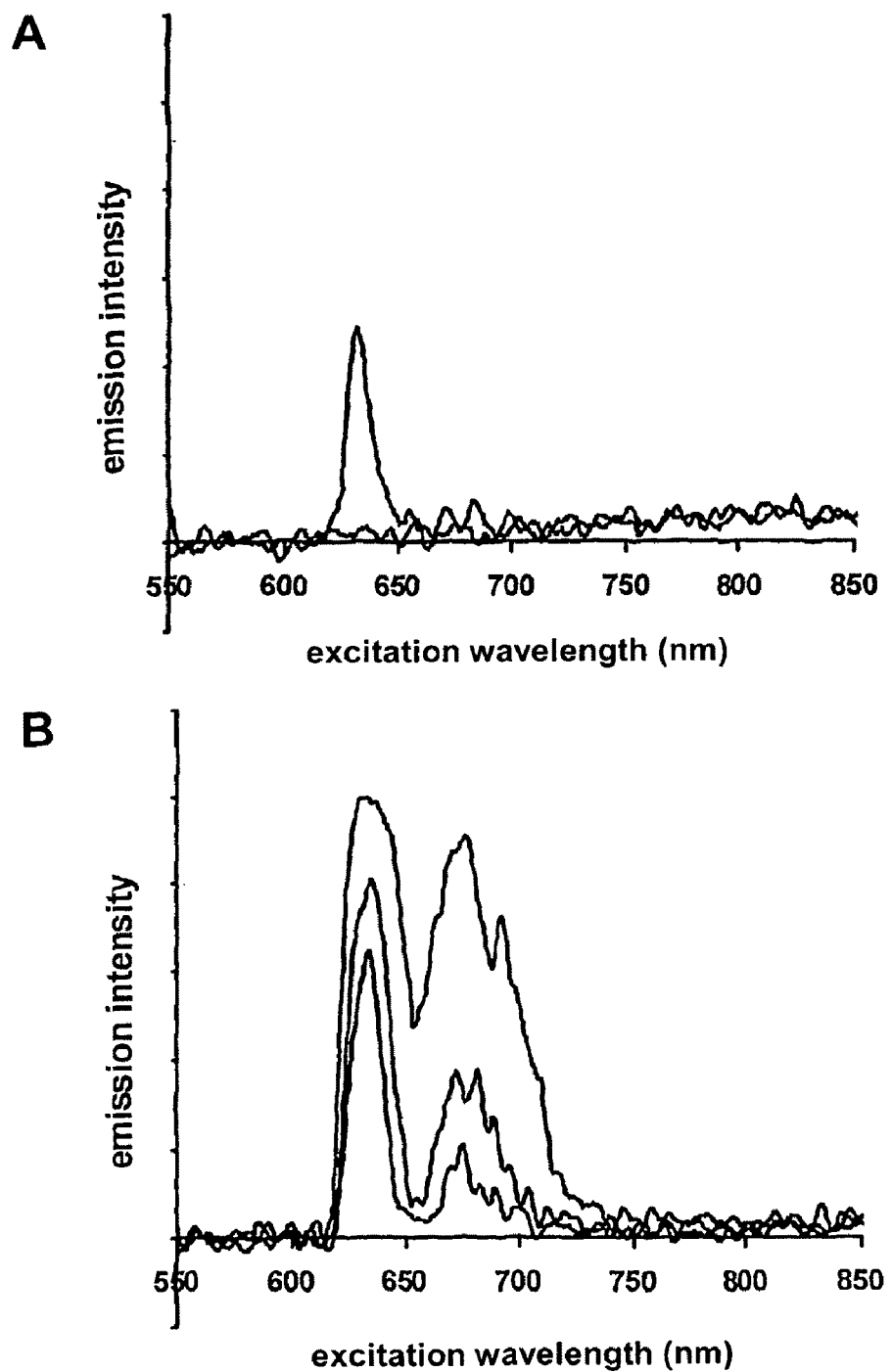
FIG. 8: Delayed luminescence spectra of PpIX bound to albumin. The emission spectra recorded at varying delays after the excitation flashes are shown. The used gate-width was 100 μs. All spectra are the result of summation of ten consecutive runs. The spectra shown in Panel A were recorded in an air-equilibrated sample. The spectra in Panel B show the increase in delayed luminescence after deoxygenation of the sample (see text for details).

To identify the type of delayed luminescence that was observed after pulsed excitation of PpIX solutions, prompt and delayed luminescence spectra were recorded. FIG. 7 shows the prompt fluorescence spectrum, with its characteristic peak at 636 nm. Delayed luminescence spectra, recorded using varying delays after the excitation flash, are shown in FIG. 8. FIG. 8, Panel A, shows the delayed luminescence in an air-saturated sample. Delayed luminescence is hardly detectable 30 µs after the excitation and is totally vanished after a delay of 100 µs. In contrast, FIG. 8, Panel B, shows that under zero oxygen conditions, delayed luminescence can be detected even after a 1 ms delay. From FIG. 8, Panel B, it is also evident that the spectrum of the delayed luminescence is qualitatively the same as the prompt fluorescence spectrum shown in FIG. 7. The red shift, characteristic for phosphorescence, is especially absent. We, therefore, identify the delayed luminescence as delayed fluorescence.

Figure 9:
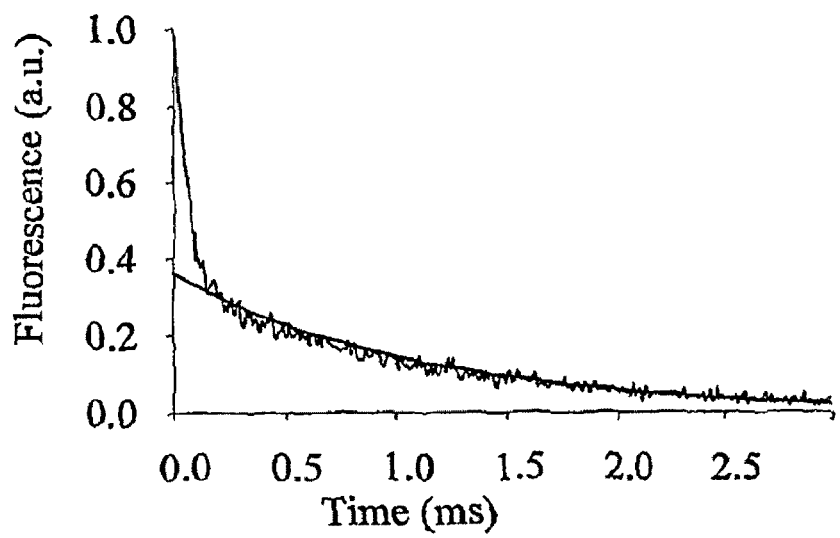
FIG. 9: Panel A: The delayed fluorescence at zero oxygen conditions measured in a solution of PpIX bound to albumin. Panel B: The Triplet-Triplet absorption at 470 nm also at zero oxygen, same sample as Panel A.
Figure 9:
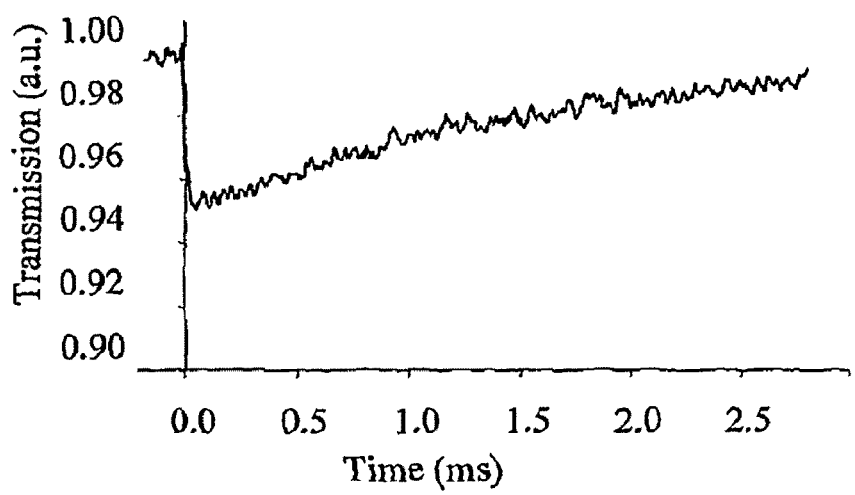

To be useful for quantitative oxygen measurements, the delayed fluorescence lifetime should be an appropriate representative of the $T_1$ lifetime. To test this, the delayed fluorescence lifetime was compared to the lifetime of transient Triplet-Triplet absorption in a deoxygenated sample. FIG. 9 shows the decay of the triplet state measured with both delayed fluorescence and Triplet-Triplet absorption. Panel A displays the decay curve measured by delayed fluorescence at 636 nm after pulsed excitation at 505 nm. The fast decaying first part of the curve is an artifact introduced by the excitation source. Panel B contains the corresponding decay trace as measured by Triplet-Triplet absorption at 470 nm.

Figure 10:
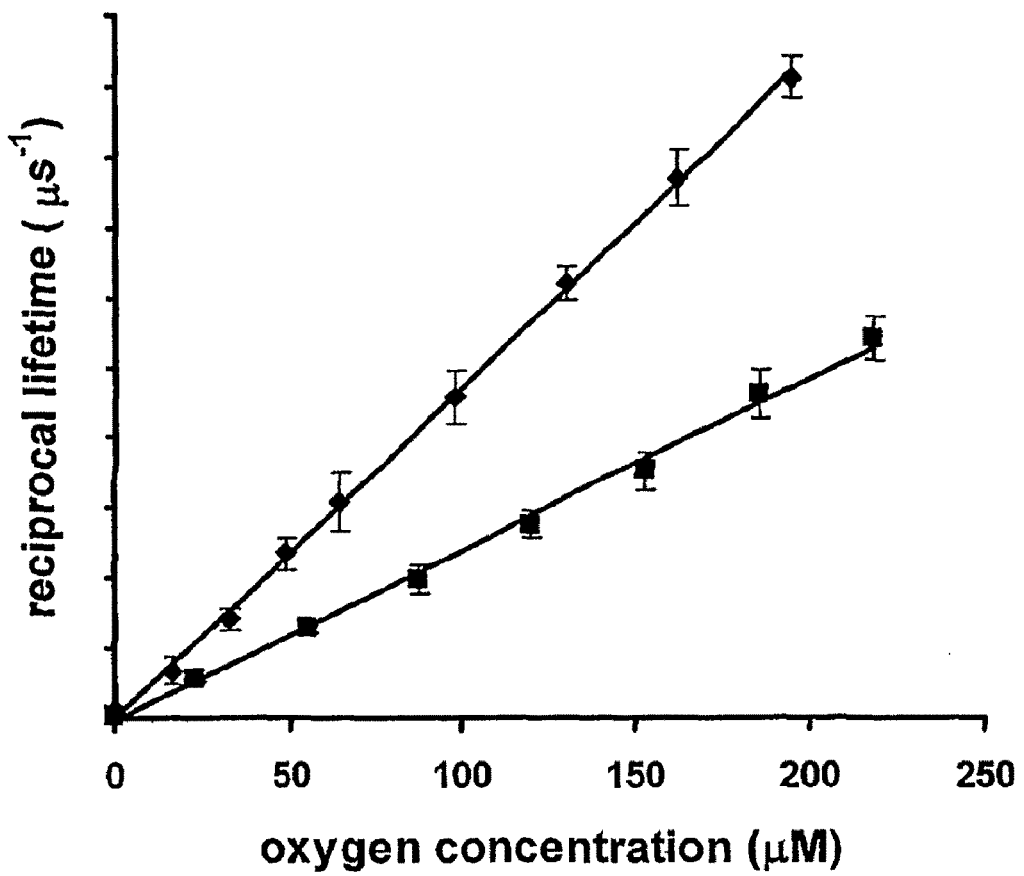
FIG. 10: Reciprocal lifetime of delayed fluorescence as a function of oxygen concentration at two different temperatures.

From FIG. 8, it is already noticeable that the lifetimes of the delayed fluorescence are highly dependable upon the oxygen concentration in the solution. A quantitative relationship between the lifetime and the oxygen concentration is mandatory if delayed fluorescence lifetimes are to be used for oxygen concentration measurements. To test the applicability of the Stern-Volmer relationship, we measured delayed fluorescence lifetimes at varying oxygen concentrations. These experiments were performed using the described reaction vessel. Starting at a high oxygen concentration (the sample was equilibrated with room air), the oxygen concentration was lowered in steps of 32.5 µM as described in the Materials and Methods section. The Stern-Volmer relationship predicts a linear relationship between the reciprocal lifetime ($1/\tau$) and the oxygen concentration. FIG. 10 shows the measured values of the reciprocal lifetime versus the oxygen concentration at 22° C. and 37° C. By performing a linear fit procedure on these data, the quenching constant $k_q$ was determined. The best-fit results are also shown in FIG. 10. At 22° C., $k_q$ was found to be 243±5 $M^{-1}$ $\mu s^{-1}$ and at 37° C., this value was 471±7 $M^{-1}$ $\mu s^{-1}$. Measured values for the decay time at zero oxygen conditions, $\tau_0$, were 1.4±0.1 ms and 1.0±0.1 ms for 22° C. and 37° C., respectively. From FIG. 10, it is clear that a good linearity between the reciprocal values of the lifetimes and the oxygen concentration exists, as is confirmed by correlation coefficients of 0.9882 and 0.9924 for 22° C. and 37° C., respectively. Moreover, no significant departure from linearity could be detected by a Runs test, providing p-values of 0.07 and 0.79 for 22° C. and 37° C., respectively. These results show that, at least over the tested oxygen concentration range, the Stern-Volmer is accurate in quantifying the relationship between the delayed fluorescence lifetimes and oxygen concentrations. As a check, a calibration experiment with a PpIX solution prepared according to the first regimen was run. The result was comparable to the calibrations performed with solutions according to the second regimen (data not shown), indicating that the reported phenomena are independent of the followed preparation procedure.

Discussion

The main findings of this study can be summarized as follows: 1) PpIX shows delayed luminescence besides the already known prompt fluorescence. 2) The emission spectrum of the delayed luminescence overlaps the spectrum of the prompt fluorescence and a red shift is absent, therefore, the delayed luminescence is classified as delayed fluorescence. 3) The lifetime of this delayed fluorescence is a representative of the lifetime of the first Triplet state. 4) Oxygen is a known quencher of the Triplet state of PpIX and this study shows that the delayed fluorescence lifetime is also oxygen dependent. 5) Moreover, it is shown that the Stern-Volmer relationship quantitatively describes the dependence of the delayed fluorescence lifetime on the oxygen concentration. These findings show that oxygen-dependent quenching of delayed fluorescence provides an exciting new method to measure oxygen concentrations, since it allows non-invasive tissue- and intracellular oxygen concentration measurements by an endogenous compound, such as, a porphyrin.

Example 2

In this example, we demonstrate the feasibility of the proposed method for measuring intramitochondrial oxygen levels in living cells.

Equipment

In this Example, a method of the invention is, for instance, performed in the time domain using pulsed excitation from an experimental high-power tunable laser. The laser of this Example consists of a doubled flash-lamp pumped Nd-YAG laser pumping an optical parametric oscillator (OPO). This results in a tunable laser providing 10 mJ pulses of 6 ns duration. The laser is coupled to a quart cuvette containing the studied samples using a glass fiber. Perpendicular to the laser beam is a detector consisting of coupling lens, monochromator and photomultiplier tube (PMT). The photomultiplier (Hamamatsu R928) is working in photon-counting mode and is gated during laser excitation by reversing the polarities of the second and third dynode. The current from the PMT is voltage converted using a fast-switching integrator (integration time 3.5 μs and reset time 0.5 μs). The voltage is digitized at a sample rate of 250 kHz using a data-acquisition board in a PC. The signal of 64 pulses is averaged before applying a mono-exponential fit procedure to the measured decay curves. The lifetime typically varies from 20 ms at high oxygen levels to 700 ms at zero-oxygen conditions.

Results

Figure 11:
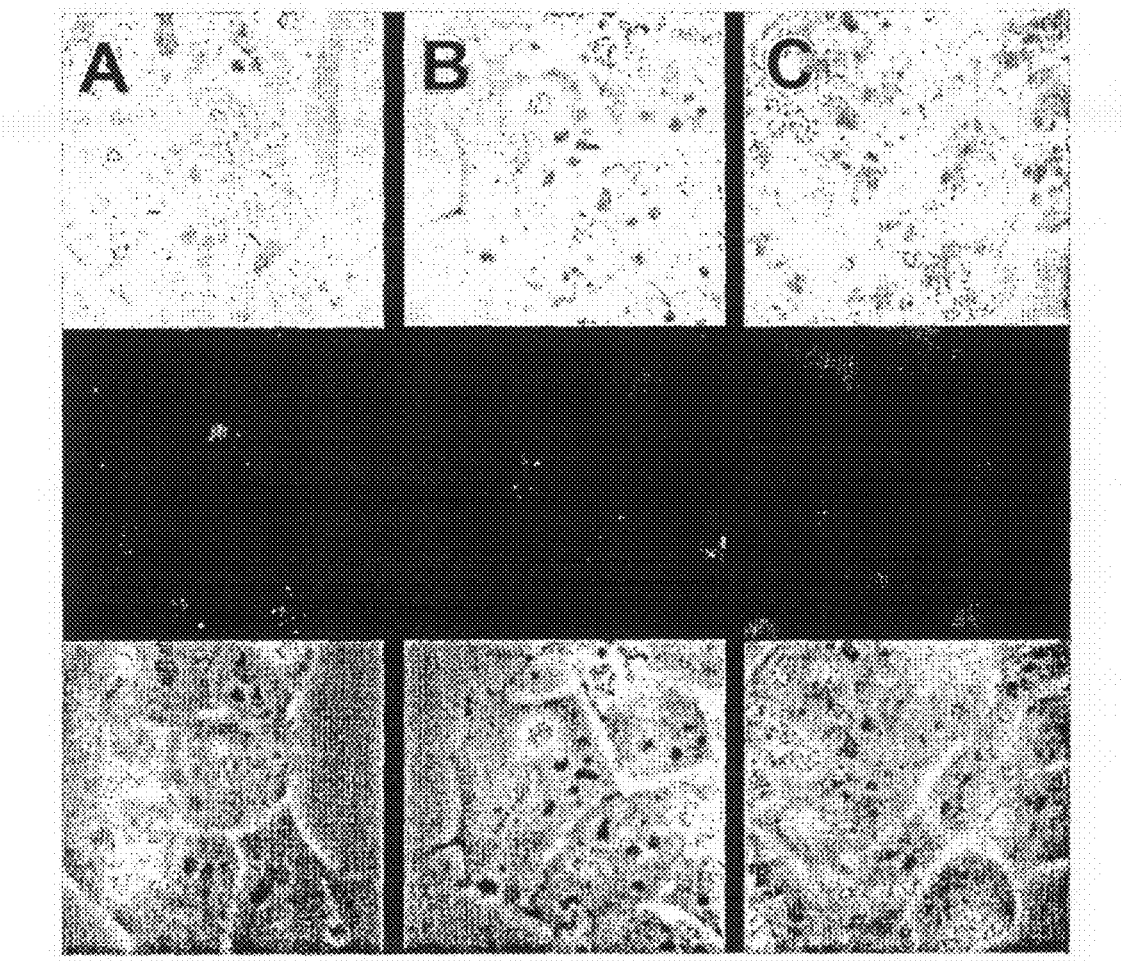
FIG. 11: Microscopy in ALA incubated neuroblastoma cells. From up to down, the image shows phase-contrast wide field, PpIX fluorescence and a combination image. Panel A: Two hours ALA incubation. Panel B: Four hours ALA incubation. Panel C: Eight hours ALA incubation.

First, the intracellular distribution of protoporphyrin IX as a function of time after the administration of 5-aminolevulinic acid (ALA) was investigated. Therefore, neuroblastoma cells were incubated with ALA during varying periods of time. Cells were observed using a Leica fluorescence microscope with appropriate filterset. FIG. 11 shows the distribution of the PpIX fluorescence at three different time points (two, four, and eight hours for Panels A, B and C, respectively). At least until four hours, the PpIX fluorescence shows a spotty appearance corresponding to a mitochondrial pattern. At eight hours, a more diffuse fluorescence is observed located in the cytosol.

Figure 12:
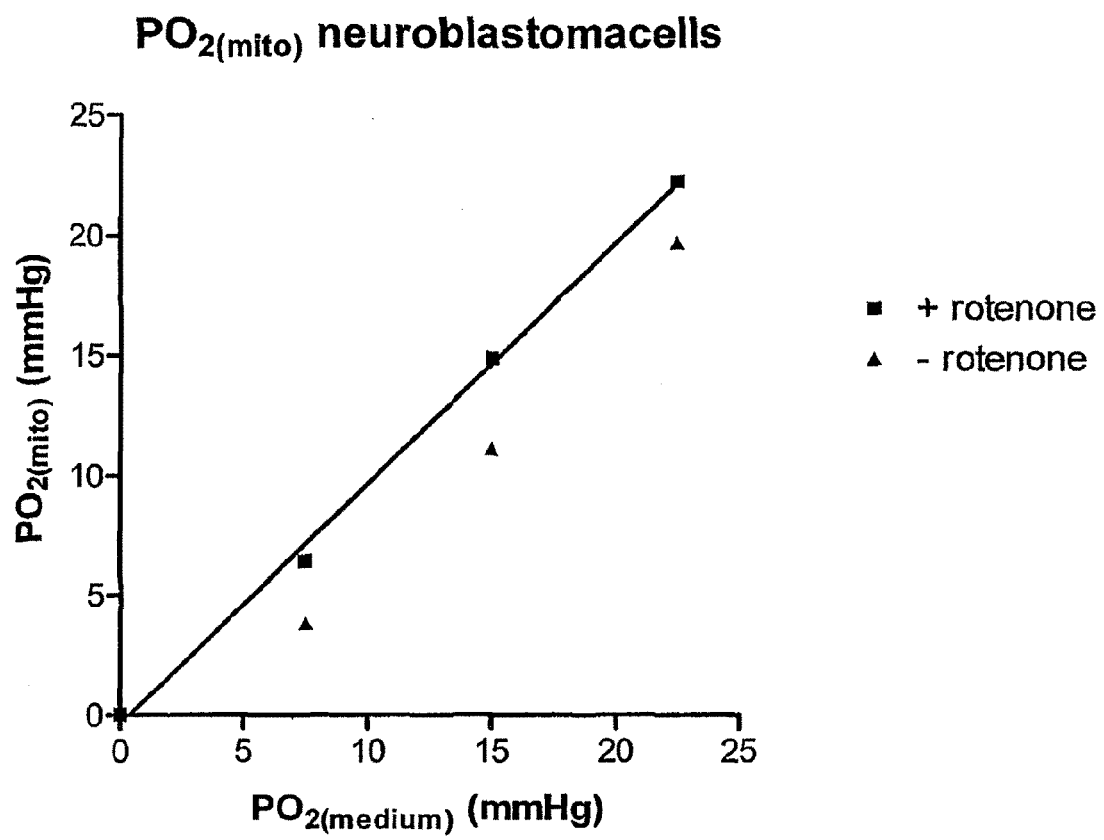
FIG. 12: Intramitochondrial oxygen measurement in a cell suspension of neuroblastoma cells. Rotenone is a blocker of the mitochondrial oxygen consumption. After administration of rotenone, the intramitochondrial $PO_2$ is assumed to be the same as the extracellular $PO_2$.

To demonstrate the ability to measure intramitochondrial oxygen levels, calibration experiments were performed in suspensions of neuroblastoma cells ($4 \times 10^6$ cells/ml) after four hours of incubation with ALA. Extracellular oxygen levels were controlled using a rotational cell oxygenator and gas flow controllers. Intramitochondrial oxygen measurements were performed before and after administration of rotenone. Rotenone is a blocker of complex 1 of the mitochondrial respiratory chain and, therefore, inhibits mitochondrial oxygen consumption. If the measurement is indeed mitochondrial of nature, adding rotenone will cause a decrease of intracellular oxygen gradients until ultimately the intramitochondrial oxygen level is the same as the extracellular oxygen level. For the measurement, this implies that adding rotenone will cause an increase in the measured intramitochondrial oxygen concentration. FIG. 12 shows the results of such a measurement. It is clear that adding rotenone causes the predicted effect, thus, the PpIX signal is mitochondrial in nature. Moreover, the signal can be calibrated, making quantitative measurements possible.

From this example, it is concluded that after administration of ALA, a time window exists in which PpIX accumulates inside the mitochondria. Moreover, it is concluded that quantitative intramitochondrial oxygen measurements are possible in living cells.

Example 3

Figure 13:
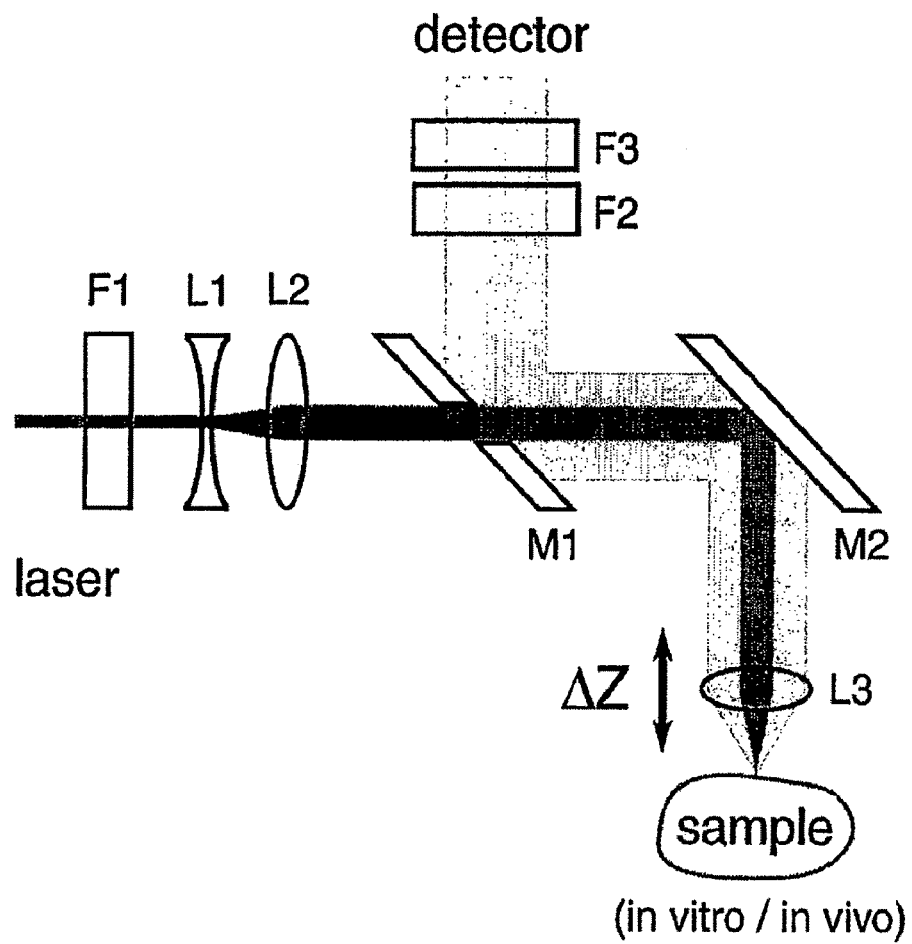
FIG. 13: Schematic diagram of the experimental set-up. The laser provided pulses of 10 ns with a wavelength of 1064 nm at a repetition rate of 10 Hz. F1 is a 1064 nm laser line bandpass filter. L1 and L2 form a beam-expander resulting in a beam width of approximately 5 mm. Mirror M1 is a standard optical mirror with a central bore-hole for passing of the laser-beam. Mirror M2 has an enhanced silver surface. L3 is a lens with a focal length of 2 cm. This distance of this lens to the sample can be varied in the z-plane (ΔZ) for adjustment of the measurement depth. Filters F2 and F3 are 700 nm bandpass filters. The detector is a red-sensitive photomultiplier tube, the output is fed into a digital oscilloscope.

An example of an experimental two-photon set-up is given in FIG. 13. In this example, excitation is achieved using a Q-switched laser operating at 1064 nm (Laser 1-2-3, Schartz Electro-Optics Inc., Orlando, Fla., USA). The laser provides pulses of approximately 10 ns duration and an energy ranging from 10 mJ per pulse for in vitro experiments to 100 mJ per pulse in in vivo experiments. The bundle diameter of the laser beam is slightly expanded to a final diameter of 5 mm by a beam expander, before being directed to the focusing lens by an optical mirror with an enhanced silver reflection surface (Opto Sigma, Santa Anna, Calif., USA). The focusing lens is a single plan-convex lens with a focal length of 2.0 cm. Based on Gaussian beam optics, the bundle diameter of 5 mm combined with a lens with a focal length of 2.0 cm results in a focal spot size of 8 μM and a focus length of 94 μm (in air). Assuming a refractive index in tissue of 1.4, the measurement volume is approximately a cylinder with diameter of 10 μm and a length of 130 μm.

The focusing lens is connected to a micrometer-screw for manual adjustment of the focal plane, thereby allowing longitudinal measurements to be made. For in vivo application, the reading of the micrometer screw is multiplied by the refractive index of tissue, assumed to be 1.4. Emission light is collected by the same lens and directed towards the photo detector by two mirrors. Selection of the phosphorescence light is achieved by two 700±20 nm bandpass filters (Oriel, Stratford, Conn., USA), positioned in series before the cathode of the photomultiplier tube (PMT, type R928, Hamamatsu, Hamamatsu City, Japan). The output of the PMT is voltage-converted by a current-to-voltage converter with subsequent wide-band amplifier (30 MHz) and fed into a digital oscilloscope (Tektronix 2440, Tektronix Inc., Beaverton, Oreg., USA). To increase signal-to-noise ratio, luminescent traces are averaged on the oscilloscope. For instance, an average of 32 traces is used. The resulting averaged traces are transferred to a computer by serial bus for data-collection and analysis using software, for instance, written in LabView (National Instruments, Austin, Tex., USA).

Example 4

Luminescence lifetimes can be measured both in the time domain as well as in the frequency domain. In the time domain, the real decay curve is measured after photo excitation with a short pulse of light. In the frequency domain, the (continuous) excitation light is modulated with a known frequency and the lifetime can be determined from the phase shift between excitation and emission light. Both methods have their specific advantages and disadvantages:

| Time domain | Frequency domain |
| --- | --- |
| Pros: | Pros: |
| No disturbance by prompt fluorescence | Lock-in amplification (high S/N-ratio) |
| No influence on oxygen tension | Relatively cheap |
| Cons: | Cons: |
| Background light needs to be taken care of Expensive | Possible disturbance by prompt fluorescence Oxygen consumption |

Technical improvements in the time domain are described below.

Optics

Figure 14:
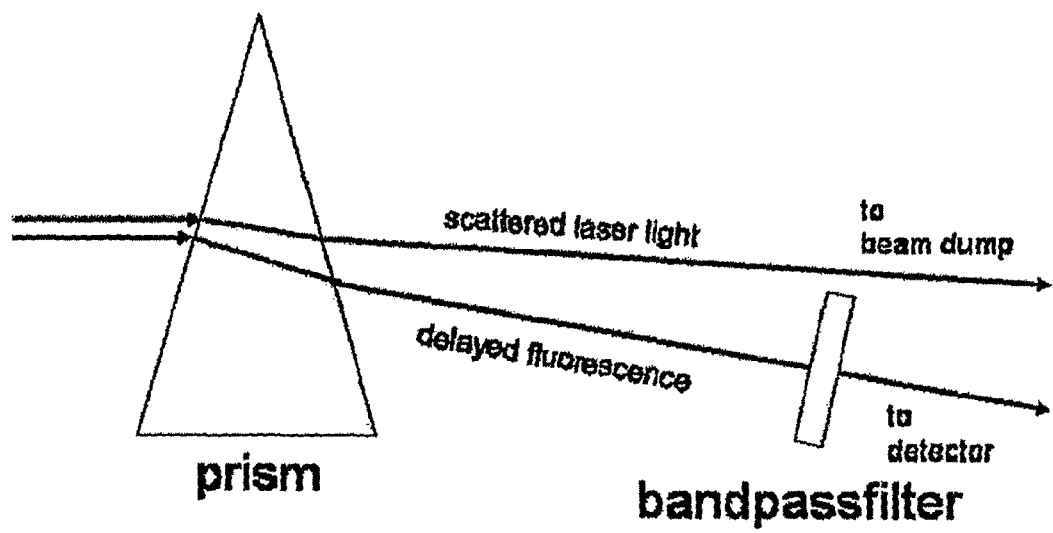
FIG. 14: A combination of a prism and a bandpass filter is a cost-effective alternative to a monochromator and provides even better transmission efficiency.

A monochromator is preferably used instead of filters in order to avoid possible disturbance of the delayed fluorescence signal as a result of fluorescence and/or phosphorescence of the filters themselves. Unfortunately, monochromators have low transmission efficiency and a gain in performance is achieved by using a different optical system. A cost-effective solution is a use of bandpass filters combined with an optical system that at least partly prevents a high amount of excitation light to reach the filters. An example of this embodiment is shown in FIG. 14.

Detectors

Considering the low signal levels, PMTs are a good. choice. Due to the high energetic laser pulse and the resulting high amount of prompt fluorescence, the detector and electronics are preferably protected against damage. In one embodiment, gating of the PMT is performed by switching the voltages of the second and third dynodes during the laser pulse. This causes distortion of the first 20 to 30 μs of the signal, diminishing adequate measurement of short lifetimes. A dedicated microchannel plate PMT is, therefore, a preferred option. An alternative is using a fast shutter in front of a standard PMT, e.g., a Pockels cell. An even cheaper alternative is the use of semiconductor devices like avalanche-photodiodes.

REFERENCES

Baxter W. T., J. M. Davidenko, L. M. Loew, J. P. Wuskell, and J. Jalife. Technical features of a CCD video camera system to record cardiac fluorescence data. *Ann. Biomed. Eng.* 25:713-725, 1997.

Bonnett R., C. Lambert, E. J. Land, P. A. Scourides, R. S. Sinclair and T. G. Truscott. The triplet and radical species of haematoporphyrin and some of its derivatives. *Photochem. Photobiol.* 38:1-8, 1983.

Carlsen H., J. O. Moskaug, S. H. Fromm, and R. Blomhoff. In vivo imaging of NF-κB activity. *J. Immunol.* 168:1441-1446, 2002.

Chantrell S. J., C. A. Mcauliffe, R. W. Munn, A. C. Pratt and E. J. Land. Excited states of protoporphyrin IX dimethyl ester: reaction of the triplet with carotenoids. *J.C.S. Faraday* 173:858-864, 1977.

Coremans J. M. C. C., C. Ince, and H. A. Bruining. NADH fluorimetry and diffuse reflectance spectroscopy on rat heart. In: *Medical Optical Tomography: Functional Imaging and Monitoring.* Edited by Müller et al. Washington, SPIE—The International Society for Optical Engineering, p. 589-617, 1993.

Coremans J. M., C. Ince, H. A. Bruining, and G. J. Puppels. (Semi-)quantitative analysis of reduced nicotinamide adenine dinucleotide fluorescence images of blood-perfused rat heart. *Biophys. J.* 72:1849-1860, 1997.

Dümmler W. Bestimmung von Hämoglobin-Oxygenierung and relativer Hämoglobin-Konzentration in biologische systemen durch auswertung von remissionsspektren met hilfe der Kubelka-Munk-theorie. Friedrich-Alexander-Universität, Erlangen-Nürnberg, 1988.

Frank K. H., M. Kessler, K. Appelbaum, and W. Dummler. The Erlangen microlightguide spectrophotometer EMPHO 1. *Phys. Med. Biol.* 34:1883-1900, 1989.

Green T. J., D. F. Wilson, J. M. Vanderkooi, and S. P. DeFeo. Phosphorimeters for analysis of decay profiles and real time monitoring of exponential decay and oxygen concentrations. *Anal. Biochem.* 174:73-79, 1998.

Hogan M. C. Phosphorescence quenching method for measurement of intracellular $pO_2$ in isolated skeletal muscle fibers. *J. Appl. Physiol.* 86 (2):720-724, 1999.

Kessler M., K. H. Frank, J. Höper, D. Tauschek, and J. Zündorf. Reflection Spectrometry. In: *Oxygen Transport to Tissue XIV.* Edited by W. Erdmann and D. F. Bruley, New York, Plenum Press, p. 203-212, 1992.

Kubelka P. and F. Munk. Ein beitrag zur optik der farbanstriche. *Z. Technische Physik* 11a:76-77, 1931.

Masters B. R. Functional imaging of cells and tissues: NADP (H) and flavoprotein redox imaging. In: *Medical Optical Tomography: Functional Imaging and Monitoring.* Edited by Müller et al. Washington, SPIE—The International Society for Optical Engineering, p. 555-575, 1993.

Mik E. G., C. Donkersloot, N. J. H. Raat, and C. Ince. Excitation pulse deconvolution in luminescence lifetime analysis for oxygen measurements in vivo. *Photochem. Photobiol.* 76:12-21, 2002.

Mik E. G., T. G. Van Leeuwen, N. J. Raat, and C. Ince. Quantitative determination of localized tissue oxygen concentration in vivo by two-photon excitation phosphorescence lifetime measurements. *J. Appl. Physiol.* 97:1962-1969, 2004.

Sato N., K. Takenobu, S. Motoaki, S. Kawano, H. Abe, and B. Hagihara. Measurement of hemoperfusion and oxygen sufficiency in gastric mucosa in vivo. *Gastroenterology* 76:814-819, 1979.

Shonat R. D., E. S. Wachman, W. Niu, A. P. Korestsky, and D. L. Farkas. Near-simultaneous hemoglobin saturation and oxygen tension maps in mouse brain using an AOTF microscope. *Biophys. J.* 73:1223-1231, 1997.

Sinclair R. S., D. Tait and T. G. Truscott. Triplet states of protoporphyrin IX and protoporphytin IX dimethyl ester. *J.C.S. Faraday I* 76:417-425, 1980.

Siegemund M., J. van Bommel, and C. Ince. Assessment of regional tissue oxygenation. *Intens. Care Med.* 25:1044-1060, 1999.

Sinaasappel M. and C. Ince. Calibration of Pd-porphyrin phosphorescence for oxygen concentration measurements in vivo. *J. Appl. Physiol.* 81:2297-2303, 1996.

Sinaasappel M., M. van Iterson, and C. Ince. Microvascular oxygen pressure in the pig intestine during hemorrhagic shock and resuscitation. *J. Physiol.* 514:245-253, 1999.

Sinclair R. S., D. Tait and T. G. Truscott. Triplet states of protoporphyrin IX and protoporphytin IX dimethyl ester. *J.C.S. Faraday I* 76:417-425, 1980.

Sterenborg H. J. C. M., M. E. Janson and M. J. C. van Gemert. A novel frequency domain fluorescence technique for determination of triplet decay times. *Phys. Med. Biol.* 44:1419-1426, 1999.

Takemura T., N. Ohta, S. Nakajima, and I. Sakata. The mechanism of photosensitization in photodynamic therapy: phosphorescence behavior of porphyrin derivatives in saline solution containing human serum albumin. *Photochem. Photobiol.* 54:683-688, 1991.

Van Bommel J., M. A. W. Maas, M. Sinaasappel, and C. Ince. Intestinal microvascular PO2 measurement with Pd-porphyrin phosphorescence in the mechanically ventilated mouse. *Ad. Exp. Med. Biol.* 454:189-193, 1998.

Vanderkooi J. M., G. Maniara, T. J. Green, and D. F. Wilson. An optical method for measurement of dioxygen concentration based upon quenching of phosphorescence. *J. Biol. Chem.* 262:5476-5482, 1987a.

Vanderkooi J. M., D. B. Calhoun, and S. W. Englander. On the prevalence or room-temperature protein phosphorescence. *Science* 236:568-569, 1987b.

Vanderkooi J. M. and J. W. Berger. Excited triplet states used to study biological macromolecules at room temperature. *Biochim. Biophys. Acta* 976:1-27, 1989.

Vanderkooi J. M., M. Erecinska, and I. A. Silver. Oxygen in mammalian tissue: methods of measurement and affinities of various reactions. *Am. J. Physiol.* 260:C1131-50, 1991.

Vinogradov S. A., M. A. Fernandez-Seara, B. W. Dupan, and D. F. Wilson. A method for measuring oxygen distributions in tissue using frequency domain phosphorometry. *Comp. Biochem. Physiol. A. Mol. Integr. Physiol.* 132:147-152, 2002.

Van Iterson M., M. Sinaasappel, K. Burhop, A. Trouwborst, and C. Ince. Low-volume resuscitation with a hemoglobin-based oxygen carrier after hemorrhage improves gut microvascular oxygenation in swine. *J. Lab. Clin. Med.* 132:421-431, 1998.

What is claimed is:

1. A method for determining a concentration of oxygen in a compartment, the method comprising:
    exciting protoporphyrin IX in the compartment, wherein protoporphyrin IX, when excited, exhibits a luminescence and/or transient absorption having a lifetime and wherein the lifetime of the luminescence and/or transient absorption is dependent on the oxygen concentration in the compartment,
    measuring the lifetime of the luminescence and/or transient absorption exhibited by protoporphyrin IX in the compartment, and
    correlating the lifetime of the luminescence and/or transient absorption with the concentration of oxygen in the compartment.

2. The method according to claim 1, wherein the luminescence and/or transient absorption comprises delayed fluorescence and/or triplet-triplet absorption.

3. The method according to claim 1, wherein the protoporphyrin IX in the compartment is photo-excited.

4. The method according to claim 1, wherein the compartment comprises a cell.

5. The method according to claim 1, wherein the compartment comprises an organelle.

6. The method according to claim 5, wherein the organelle comprises a mitochondrion.

7. The method according to claim 1, wherein the compartment comprises at least part of a tissue.

8. The method according to claim 1, wherein the compartment comprises an organ.

9. The method according to claim 1, wherein the compartment comprises a tumor.

10. The method according to claim 1, wherein the compartment comprises microcirculation.

11. The method according to claim 1, wherein the compartment is present in a culture medium.

12. The method according to claim 1, wherein the compartment comprises a cell suspension.

13. The method according to claim 1, wherein the lifetime of the luminescence and/or transient absorption is compared with a reference.

14. The method according to claim 1, wherein the lifetime of the luminescence and/or transient absorption is measured in the time-domain.

15. The method according to claim 1, wherein the lifetime of the luminescence and/or transient absorption is measured in the frequency-domain.

16. The method according to claim 1, wherein multi-photon excitation is applied.

17. The method according to claim 1, wherein two-photon excitation is applied.

18. The method according to claim 1, wherein a precursor of protoporphyrin IX is administered to the compartment, which precursor is able to be converted into at least protoporphyrin IX, and wherein the protoporphyrin IX derived from the precursor is excited.

19. The method according to claim 18, wherein the lifetime of the luminescence and/or transient absorption is measured within four hours of administering precursor of protoporphyrin IX to the compartment.

20. The method according to claim 18, wherein the precursor is 5-aminolevulinic acid.

21. The method according to claim 1, wherein the protoporphyrin IX is excited by a device comprising:
    means for exciting protoporphyrin IX in the compartment, and
    means for measuring the lifetime of the luminescence and/or transient absorption in the compartment,
    and further wherein said device measures the lifetime of the luminescence and/or transient absorption in the compartment.

22. A method for determining the concentration of oxygen in a compartment, said compartment selected from the group consisting of a cell, an organelle, a mitochondrion, a tissue, an organ, a tumor, and microcirculation, the method comprising:
    exciting, in the compartment, protoporphyrin IX, wherein protoporphyrin IX, when excited, exhibits luminescence and/or transient absorption having a lifetime, wherein the lifetime of the luminescence and/or transient absorption is dependent on the oxygen concentration in the compartment,
    measuring the lifetime of the luminescence and/or transient absorption exhibited by protoporphyrin IX in the compartment,
    comparing the measured lifetime of the luminescence and/or transient absorption exhibited by protoporphyrin IX in the compartment with a reference, and
    correlating the measured lifetime of the luminescence and/or transient absorption exhibited by protoporphyrin IX compartment with the concentration of oxygen in the compartment.

* * * * *

UNITED STATES PATENT AND TRADEMARK OFFICE
CERTIFICATE OF CORRECTION

PATENT NO. : 8,008,038 B2  Page 1 of 1
APPLICATION NO. : 12/584691
DATED : August 30, 2011
INVENTOR(S) : Egbert G. Mik and Michiel Sinaasappel It is certified that error appears in the above-identified patent and that said Letters Patent is hereby corrected as shown below:

On the Title Page
In ITEM (56) References Cited
Page 1, Column 2, line 20    change "reaction nfo" to --reaction of--

In the claims:
Claim 22, Column 24, lines 61,62,    change "IX compartment" to --IX in the compartment--

Signed and Sealed this
Thirteenth Day of November, 2012

David J. Kappos
*Director of the United States Patent and Trademark Office*